United States Patent [19]

Goto et al.

[11] Patent Number: 5,025,033

[45] Date of Patent: Jun. 18, 1991

[54] ALKYLENE DIAMINES

[75] Inventors: Giichi Goto, Osaka; Akinobu Nagaoka, Kawanishi, both of Japan

[73] Assignee: Takeda Chemical Industries, Ltd., Osaka, Japan

[21] Appl. No.: 301,065

[22] Filed: Jan. 25, 1989

[30] Foreign Application Priority Data

Jan. 29, 1988 [JP] Japan ................................. 63-021009
May 10, 1988 [JP] Japan ................................. 63-114360

[51] Int. Cl.[5] ...................... A61K 31/40; C07D 487/02; C07D 209/48; C07C 233/64
[52] U.S. Cl. ..................................... 514/417; 514/211; 514/615; 540/523; 548/472; 548/477; 564/161; 564/166; 564/176
[58] Field of Search ................. 548/472, 477; 514/211, 514/417, 615; 540/523; 564/161, 166, 176

[56] References Cited

U.S. PATENT DOCUMENTS

| | | | |
|---|---|---|---|
| 2,343,198 | 2/1944 | Moore | 544/168 |
| 2,759,933 | 8/1956 | Speeter | 544/169 |
| 2,759,934 | 8/1956 | Speeter | 548/477 |
| 2,819,305 | 1/1958 | Lott et al. | 565/176 |
| 3,898,214 | 8/1975 | Vogt et al. | 540/523 |
| 4,080,449 | 3/1978 | Croisier et al. | 514/213 |
| 4,238,395 | 12/1980 | Buckler et al. | 548/477 |

FOREIGN PATENT DOCUMENTS

| | | |
|---|---|---|
| 0065229 | 11/1982 | European Pat. Off. . |
| 0109636 | 5/1984 | European Pat. Off. . |
| 0138198 | 4/1985 | European Pat. Off. . |
| 0142283 | 5/1985 | European Pat. Off. . |
| 326106 | 8/1989 | European Pat. Off. . |
| 3242344 | 5/1984 | Fed. Rep. of Germany . |
| 6902 | 6/1969 | France . |

OTHER PUBLICATIONS

Manoury et al., "Synthesis and Antihypertensive ...", J. Med. Chem. 29 19–25 (1986).
CA 96:68518n, 1981, Borisova et al., "Synthesis of New Aliphatic-Aromatic Aminobutylamides...".
CA 84: 135338w, 1976, Borisova et al., "(Dimethylamino)Phenylbutyl Amides".
Kalman Hideg et al., "A New Group of Antifibrillants, N-(Omega-Aminoalkyl)phthalimides", Journal of Medicinal Chemistry, vol. 8, Mar. 1965, pp. 257–259.
Annual Reports in Medicinal Chemistry, 1988, "Agents for the Treatment of Cognitive Disorders", Mattson et al., pp. 29–38.
Drug Development Research 12:163, 1988, Mechanisms of Cholinesterase Inhibition in Senile Dementia of the Alzheimer Type: Clinical, Pharmacological, and Therapeutic Aspects, Becker et al., FASEB JNL., 1989.
New England Journal of Medicine, "Oral Tetrahydroaminoacridine in Long-Term Treatment of Senile Dementia, Alzheimer Type", Summers et al., vol. 315, No. 20, Nov. 13, 1986.
European Journal of Pharmacology, 1988, "Tetrahydraminoacridine Selectively Attenuates NMDA Receptor-Mediated Neurotoxicity", Davenport et al., pp. 73–78.
Pharmacologist, (30, No. 3, A25, 1988), Whetzel et al.
Derwent Abstract of Japanese Patent Appln. Laid-Open No. 227565 (Eisai) (J6 1227-565-A).

Primary Examiner—Jane T. Fan
Assistant Examiner—Celia Chang
Attorney, Agent, or Firm—Wegner, Cantor Mueller & Player

[57] ABSTRACT

A cholinesterase inhibiting agent which contains an alkylene diamine of the formula

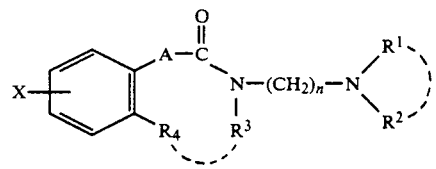

wherein $R^1$ and $R^2$ each independently is a hydrogen atom or a hydrocarbon residue which may optionally be substituted, or $R^1$ and $R^2$ combinedly form, together with the adjacent nitrogen atom, a condensed heterocyclic group, $R^3$ is a hydrogen atom or a hydrocarbon residue or an acyl group which may optionally be substituted and $R^4$ is a hydrogen atom, or $R^3$ and $R^4$ combinedly form a group of the formula

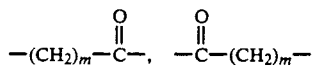

or $-(CH_2)_{m+1}-$ (m being 0, 1 or 2), A is $-(CH_2)_l-$ (l being 0, 1 or 2) or $-CH=CH-$, X is a substituent or substituents and n is an integer of 4 to 7, or a salt thereof, which are useful as cerebral function improving agents for the prevention or treatment of senile dementia, Alzheimer's disease, Huntington's chorea, hyperkinesia, mania and so forth.

13 Claims, No Drawings

ALKYLENE DIAMINES

This invention relates to alkylene diamines useful as drugs, in particular cerebral function improving agents in the treatment of senile dementia, Alzheimer's disease or the like.

As the average life span of people has been increasing, various compounds having cerebral function improving activity have been proposed. Among them, physostigmine, which is a cholinesterase inhibitor, has been demonstrated to have cerebral function improving activity. On the other hand, in the Journal of Medicinal Chemistry, 8, 257 (1965) and Acta Physiologica Academiae Scientiarum Hungaricae, 26, 287 (1965), there is disclosed a compound of the formula

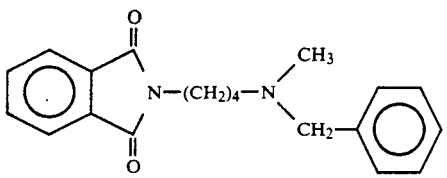

with a statement that said compound has antifibrant activity (antifibrillatory activity, antiarrhythmic activity), but there is no mention of cholinesterase inhibiting activity.

The above-mentioned representative cholinesterase, physostigmine, has drawbacks. For instance, its activity is of short duration and its toxicity is high.

It is an object of the invention to provide compounds more potent in activity, longer in activity duration and lower in toxicity as compared with prior art compounds known to have cerebral function improving activity. Compounds of the general formula

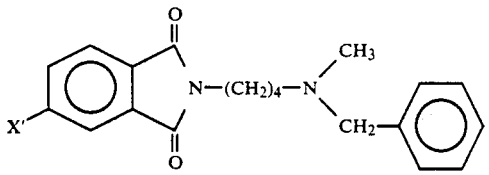

in which X' is an appropriate substituent (e.g. nitro, etc.) have potent cholinesterase inhibiting activity.

Alkyene diamines of the formula

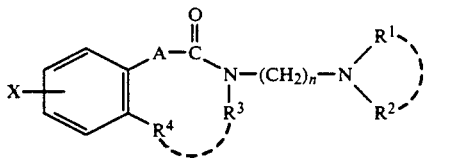

wherein $R^1$ and $R^2$ each independently is a hydrogen atom or a hydrocarbon residue which may optionally be substituted, or $R^1$ and $R^2$ combinedly form, together with the adjacent nitrogen atom, a condensed heterocyclic group, $R^3$ is a hydrogen atom or a hydrocarbon residue or an acyl group each of which may optionally be substituted, and $R^4$ is a hydrogen atom, or $R^3$ and $R^4$ combinedly form a group of the formula

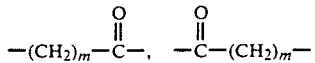

or $-(CH_2)_{m+1}-$ (m being 0, 1 or 2), A is $-(CH_2)_l-$ (l being 0, 1 or 2) or $-CH=CH-$, X is a substituent or substituents and n is an integer of 4 to 7, and salts thereof showed good cerebral function improving activity.

Among the alkylene diamines of the formula (I), the compounds of the formula

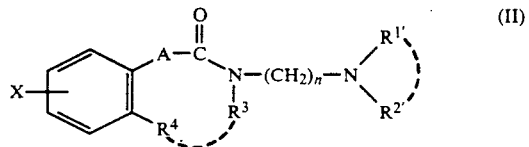

wherein $R^{1'}$ is a hydrogen atom or a lower alkyl group which may be substituted by hydroxy group, $R^{2'}$ is an α-aralkyl group which may be substituted, and other symbols are as defined above for the formula (I), and salts thereof are novel compounds. The present inventors succeeded in establishing synthetic method for these novel compounds and obtaining them.

Thus, the invention provides novel compounds of the formula (II) [hereinafter sometimes referred to briefly as compound (II)] and salts thereof, methods of producing the same, cholinesterase inhibiting agents containing the compound of the formula (I) [hereinafter sometimes referred to briefly as compound(I)] and cerebral function improving agents containing the same.

Referring to the above formula (I) and (II), the "hydrocarbon residue" in the definition "hydrocarbon residue, which may optionally be substituted" given for $R^1$, $R^2$ and $R^3$ includes, among others, hydrocarbon residues which are acyclic or cyclic, saturated or unsaturated as well as residues resulting from various combinations of such hydrocarbon residues. As acyclic saturated hydrocarbon residues, there may be mentioned, for example, straight or branched $C_{1-11}$ alkyl groups (e.g. methyl, ethyl, n-propyl, i-propyl, n-butyl, i-butyl, tert-butyl, n-pentyl, n-hexyl).

As acyclic unsaturated hydrocarbon residues, there may be mentioned straight or branched $C_{2-4}$ alkenyl groups (e.g. vinyl, allyl, 2-butenyl) and straight or branched $C_{2-4}$ alkynyl groups (e.g. propargyl, 2-butynyl).

As cyclic saturated hydrocarbon residues, there may be mentioned monocyclic $C_{3-7}$ cycloalkyl groups (e.g. cyclobutyl, cyclopentyl, cyclohexyl) and bridged saturated $C_{8-14}$ hydrocarbon residues [e.g. bicyclo[3.2.1]oct-2-yl, bicyclo[3.3.1]non-2-yl, adamantan-1-yl]. As cyclic unsaturated hydrocarbon residues, there may be mentioned phenyl, naphthyl and the like.

As the substituents on these hydrocarbon residues, there may be mentioned halogen atoms (e.g. chlorine, bromine, iodine); nitro; nitrile (cyano); hydroxy; $C_{1-4}$ alkoxy groups (e.g. methoxy, ethoxy, propyloxy, butyloxy, isopropyloxy); $C_{1-4}$ alkylthio groups (e.g. methylthio, ethylthio, propylthio, isopropylthio, butylthio); amino; mono- or di-$C_{1-4}$-alkyl-substituted amino groups (e.g. methylamino, ethylamino, propylamino, dimethylamino, diethylamino); $C_{1-4}$ alkoxycarbonyl groups (e.g. methoxycarbonyl, ethoxycarbonyl, propoxycarbonyl, isobutoxycarbonyl), hydroxycarbonyl (carboxy); $C_{1-6}$ alkylcarbonyl groups (e.g. methylcarbonyl, ethylcarbonyl, butylcarbonyl, cyclohexylcarbonyl); carbamoyl; mono- or di-$C_{1-4}$ alkyl-substituted carbamoyl groups (e.g. methylcarbamoyl, ethylcarbamoyl, propylcarbamoyl, butylcarbamoyl, diethylcarbamoyl, dibutylcarbamoyl); phenyl, naphthyl, benzoyl, phenoxycarbonyl, phenyl-$C_{1-4}$ alkylcarbamoyl and phenylcarbamoyl groups, which may optionally have 1 to 4 substituents [each substituent on the phenyl or naphthyl group being, for example, $C_{1-4}$ alkyl, such as methyl, ethyl, propyl, butyl or isopropyl, phenyl, which may optionally have 1 to 4 substitutents (each substituent on said phenyl group being, for example, $C_{1-4}$ alkyl, such as methyl, ethyl, propyl, butyl or isopropyl, $C_{1-4}$ alkoxy such as methoxy, ethoxy, propoxy or butoxy, halogen, such as chlorine, bromine or iodine, hydroxy, benzyloxy, amino, mono- or di-$C_{1-4}$ alkyl-substituted amino, nitro or $C_{1-4}$ alkoxycarbonyl),-halogen, such as chlorine, bromine or iodine, hydroxy, benzyloxy, amino, nitro or $C_{1-4}$ alkoxycarbonyl]; and adamantan-1-yl.

The number of these substituents on the hydrocarbon residues is suitably about 1 to 3.

Further referring to the above formula (I), $R^1$ and $R^2$ may form, together with the adjacent nitrogen atom, a condensed heterocyclic group, which may optionally be substituted. As the "condensed heterocycle" referred to in this definition "condensed heterocyclic group, which may optionally be substituted", there may be mentioned, for example, 1,2,3,4-tetrahydroquinoline, 1,2,3,4-tetrahydroisoquinoline, 1,2,3,4,5,6,7,8-octahydroisoquinoline, indoline and isoindoline. As the substituents on such condensed heterocyles, there may be mentioned $C_{1-4}$ alkyl groups, such as methyl, ethyl, propyl, isopropyl and butyl, halogen atoms, such as chlorine, bromine and iodine, a hydroxy group, $C_{1-4}$ alkyloxy groups, such as methoxy, ethoxy, propyloxy, isopropyloxy and butyloxy, an amino group, mono- or di-$C_{1-4}$ alkyl-substituted amino groups, such as methylamino and dimethylamino, a nitro group, a nitrile group, and $C_{1-4}$ alkoxycarbonyl groups, such as methoxycarbonyl.

As the lower alkyl groups represented by $R^{1'}$ in the above formula (II), there may be mentioned, for example, straight or branched $C_{1-6}$ alkyl groups such as methyl, ethyl, n-propyl, i-propyl, n-butyl, i-butyl tert-butyl and pentyl.

The α-aralkyl groups represented by $R^{2'}$ in the formula (II) designate alkyl groups substituted by a cylic unsaturated hydrocarbon residue at the α-position. As the alkyl groups and the cyclic unsaturated hydrocarbon residues in the α-aralkyl groups, the above-mentioned alkyl groups and the cyclic unsaturated hydrocarbon residues for $R^1$, $R^2$ and $R^3$ are applicable. Specifically, examples of the α-aralkyl groups represented by $R^{2'}$ are benzyl, naphthylmethyl, 1-phenylethyl, benzhydryl and so forth.

The cyclic unsaturated hydrocarbon residue of these α-aralkyl group may have one or more, preferably one to four, substituent(s). As the substituent(s) on the cyclic unsaturated hydrocarbon residue, there may be mentioned the substituents that have been mentioned hereinabove as substituents on the hydrocarbon residue.

As the acyl group represented by $R^3$ in the above formula (I) and (II), there may be mentioned, for example, a carboxylic acid-derived acryl group, a carbamic acid-derived acyl group, a sulfonic acid-derived acyl group, a substituted oxycarboxylic acid-derived acyl group and the like. These acyl groups may have a substituent or subtituents.

The carboxylic acid-derived acyl group includes, among others, $C_{1-6}$ alkylcarbonyl groups, such as acetyl, propionyl, butyryl, valeryl, hexanoyl, isobutyryl and isovaleryl, $C_{3-8}$ cycloalkylcarbonyl groups, such as cyclopentylcarbonyl and cyclohexylcarbonyl, $C_{3-8}$ cycloalkyl-$C_{1-6}$ alkylcarbonyl groups, such as cyclopentylacetyl, $C_{2-6}$ alkenyl- or alkynylcarbonyl groups, such as acryloyl, crotonyl, 2-pentenoyl, 4-pentynoyl, 2-hexenonyl, 3-hexenoyl and 2,4-hexadienoyl, and arylcarbonyl groups, such as benzoyl and naphthoyl.

The carbamic acid-derived acyl group includes, among others, carbamoyl and mono- or di-substituted carbamoyl groups. Said mono- or di-substituted carbamoyl groups are, for example, mono- or di-$C_{1-4}$ alkylcarbamoyl groups, such as methylcarbamoyl, ethylcarbamoyl, propylcarbamoyl, butylcarbamoyl, dimethylcarbamoyl, diethylcarbamoyl and dipropylcarbamoyl, mono- or di-$C_{3-6}$ alkenyl- or alkynylcarbamoyl groups, such as allylcarbamoyl, 3-butenylcarbamoyl, 4-pentenylcarbamoyl and diallylcarbamoyl, and aromatic group-substituted carbamoyl groups, such as phenylcarbamoyl, naphthylcarbamoyl and diphenylcarbamoyl.

The sulfonic acid-derived acyl group includes among others, inorganic sulfonyl groups, such as sodium sulfonate group, $C_{1-6}$ alkylsulfonyl groups, such as methylsulfonyl, ethylsufonyl, propylsulfonyl and butylsulfonyl, $C_{2-6}$ alkenyl- or alkynylsulfonyl groups, such as allylsulfonyl and 2-methyl-2-propenylsulfonyl, and aromatic sulfonyl groups, such as phenylsulfonyl and naphthylsulfonyl.

The substituted oxycarboxylic acid-derived acyl group includes, among others, $C_{1-6}$ alkyloxycarbonyl groups, such as methyloxycarbonyl, ethyloxycarbonyl, tert-butyloxycarbonyl and hexyloxycarbonyl, $C_{3-8}$ cycloalkyloxycarbonyl groups, such as cyclopentyloxycarbonyl and cyclohexyloxycarbonyl, cycloalkylalkyloxycarbonyl groups, such as cyclopentanemethyloxycarbonyl, $C_{2-7}$ alkenyl- or alkynyloxycarbonyl groups, such as allyloxycarbonyl, crotyloxycarbonyl and 2-penten-1-oxycarbonyl, and aromatic or araliphatic hydrocarbyloxycarbonyl groups, such as phenyloxycarbonyl and benzyloxycarbonyl.

When these acyl groups are further substituted, each substituent may be one of those substituents that have been mentioned hereinabove as substituents on the hydrocarbon residues.

As for the stereochemistry of —CH=CH— represented by A in the above formulae (I) and (II), the configuration of the compound of formulae (I) and (II) may be E or Z or the compound may be a mixture of E and Z isomers.

X in the formulae (I) and (II) designates a substituent or substituents on the benzene ring. That is, the benzene ring has one or more substituent(s) selected from the substituents mentioned below for X.

The substituent(s) represented by X includes $C_{1-4}$ alkyl groups (e.g. methyl, ethyl, propyl, butyl, etc.); halogen atoms (e.g. chlorine, bromine, iodine, etc.); nitro; nitrile; hydroxy; $C_{1-4}$ alkoxy groups (e.g. methoxy, ethoxy, propyloxy, butyloxy, isopropyloxy, etc.); $C_{1-4}$ alkylthio groups (e.g. methylthio, ethylthio, propylthio, isopropylthio, butylthio, etc.); amino; mono- or di-$C_{1-4}$ alkyl-substituted amino groups (e.g. methylamino, ethylamino, propylamino, dimethylamino, diethylamino, etc.); $C_{1-4}$ alkylcarbonylamino groups (e.g. acetylamino, propionylamino, butyrylamino, etc.); $C_{1-4}$ alkylsulfonylamino groups (e.g. methylsulfonylamino, ethylsulfonylamino, propylsulfonylamino, etc.); $C_{1-4}$ alkoxycarbonyl groups (e.g. methoxycarbonyl, ethoxycarbonyl, propoxycarbonyl, isobutoxycarbonyl, etc.); hydroxycarbonyl; $C_{1-6}$ alkylcarbonyl groups (e.g. methylcarbonyl, ethylcarbonyl, butylcarbonyl, cyclohexylcarbonyl, etc.); carbamoyl; mono- or di-$C_{1-4}$ alkyl-substituted carbamoyl groups (e.g. methylcarbamoyl, ethylcarbamoyl, propylcarbamoyl, butylcarbamoyl, diethylcarbamoyl, dibutylcarbamoyl, etc.); $C_{1-6}$ alkylsulfonyl (e.g. methylsulfonyl, ethylsulfonyl, propylsulfonyl, cyclopentylsulfonyl, cyclohexylsulfonyl, etc.); and phenyl, phenoxy, benzoyl, phenoxycarbonyl, phenyl-$C_{1-4}$ alkylcarbamoyl, phenylcarbamoyl, phenyl-$C_{1-4}$ alkylcarbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino and phenylsulfonylamino groups, which may optionally have 1 to 4 substituents (each substituent on the phenyl group being, for example, $C_{1-4}$ alkyl, such as methyl, ethyl, propyl, butyl or isopropyl, halogen, such as chlorine, bromine or iodine, hydroxy, benzyloxy, amino, mono- or di-$C_{1-4}$ alkyl-substituted amino, such as methylamino or dimethylamino, nitro, or $C_{1-4}$ alkoxycarbonyl).

Preferred examples of the compound of the above formulae (I) and (II) are now described. Thus, in preferred embodiments, $R^1$ and $R^2$ each independently is a hydrogen atom, a $C_{1-6}$ alkyl group, such as methyl, ethyl or propyl, a benzyl group or a naphthylmethyl group or $R^1$ and $R^2$, together with the adjacent nitrogen atom, form an isoindoline or 1,2,3,4-tetrahydroisoquinoline ring. In particularly preferred embodiments, $R^2$ is a benzyl group which may have, as the substituents one or two methyl, methoxy, fluorine and/or chlorine and $R^1$ is a $C_{1-4}$ alkyl group, particularly ethyl.

As for $R^{1'}$ and $R^{2'}$, particularly preferred are the compounds of the formula (II) wherein $R^{1'}$ is ethyl and $R^{2'}$ is a benzyl group which may be substituted by methyl, methoxy, chlorine and/or fluorine, the number of the substituent(s) being preferably one or two.

As regards $R^3$ and $R^4$, $R^3$ is preferably a hydrogen atom, a $C_{1-6}$ alkyl group, such as methyl, ethyl or propyl, an aromatic group, such as phenyl, a $C_{1-6}$ alkylcarbonyl group, such as acetyl, propionyl or butyryl, or an arylcarbonyl group, such as benzoyl, while $R^4$ is preferably a hydrogen atom; or, taken combinedly, $R^3$ and $R^4$ preferably form a group of the formula

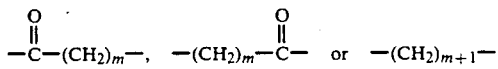

which m is an integer of 0, 1 or 2. In particularly preferred embodiments, $R^3$ is a hydrogen atom, a $C_{1-4}$ alkyl group or a $C_{1-4}$ alkylcarbonyl group and $R^4$ is a hydrogen atom, or $R^3$ and $R^4$ combinedly form the group

A is preferably a bond or the group —CH=CH—.

In preferred embodiments, X is a $C_{1-4}$ alkyl group, such as methyl, ethyl or propyl, a halogen atom, such as chlorine or bromine, a nitro group, a nitrile group, a $C_{1-4}$ alkoxy group, such as methoxy, ethoxy or propyloxy, a substituted or unsubstituted phenoxy group, a $C_{1-4}$ alkylcarbonyl amino group, such as acetylamino or propionylamino, a $C_{1-4}$ alkylsulfonylamino group, such as methylsulfonylamino or ethylsulfonylamino, a phenyl-$C_{1-4}$ alkylsulfonylamino group, such as benzylsulfonylamino, a substituted or unsubstituted phenylsulfonylamino group, a $C_{1-4}$ alkylcarbonyl group, such as methylcarbonyl, ethylcarbonyl or butylcarbonyl, a $C_{1-4}$ alkoxycarbonyl group, such as methoxycarbonyl, ethoxycarbonyl or butoxycarbonyl, a substituted or unsubstituted phenoxycarbonyl group, a substituted or unsubstituted benzoyl group, carbamoyl, a mono- or di-$C_{1-4}$ alkyl-substituted carbamoyl group, such as methylcarbamoyl, ethylcarbamoyl or butylcarbamoyl, a substituted or unsubstituted phenylcarbamoyl group, a $C_{1-4}$ alkylthio such as methylthio, ethylthio or propylthio, a substituted or unsubstituted phenyl $C_{1-4}$ alkylthio, a $C_{1-6}$ alkylsulfinyl such as methylsulfinyl, ethylsulfinyl or propyl sulfinyl, a substituted or unsubstituted phenyl $C_{1-4}$ alkyl sulfinyl, a $C_{1-6}$ alkylsulfonyl group, such as methylsulfonyl, propylsulfonyl or cyclohexylsulfonyl, a substituted or unsubstituted phenyl-$C_{1-4}$ alkylsulfonyl group, a substituted or unsubstituted phenyl group, or a substituted or unsubstituted phenyl-$C_{1-4}$ alkyl group, such as benzyl or substituted benzyl. In particularly preferred embodiments, X is nitro, amino, acetylamino, $C_{1-4}$ alkoxy, substituted or unsubstituted phenyl, substituted or unsubstituted benzyl, substituted or unsubstituted benzoyl, substituted or unsubstituted benzoylamino, $C_{1-6}$ alkylsulfinyl, $C_{1-6}$ alkylsulfonyl, substituted or unsubstituted benzylsulfonyl, substituted or unsubstituted phenylsulfonylamino, substituted or unsubstituted benzylsulfonylamino, substituted or unsubstituted phenylcarbamoyl-, methoxycarbonyl, diethylcarbamoyl or the like.

Those compounds whose benzene ring has, as the substituent(s) X, one substituent or two, the same or different, substituents of the above-mentioned substitutents, particularly one substituent, are particularly preferred.

n is preferably 4, 5 or 6. Particularly, 4 or 5 is preferred as n.

In further particularly preferred examples of the compound according to the invention, in formula (I) or (II), $R^1$ or $R^{1'}$ is a $C_{1-4}$ alkyl group, such as methyl or ethyl, $R^2$ or $R^{2'}$ is a benzyl group, $R^3$ and $R^4$ combinedly form the group

or $R^3$ is a $C_{1-6}$ alkylcarbonyl group or an arylcarbonyl group and $R^4$ is a hydrogen atom, A is a bond or —CH=CH—, n is 4, 5 or 6, and X is one group or two groups which are the same or different selected from nitro, amino, benzoylamino, methoxy, hydroxy, methylsulfonyl, acetylamino and carboxyl group.

The compounds (I) and (II) according to the invention may be in the form of acid addition salts, preferably pharmaceutically acceptable acid addition salts. As such salts, there may be mentioned, for example, salts with inorganic acids (e.g. hydrochloric acid, nitric acid, phosphoric acid, hydrobromic acid, sulfuric acid) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

In cases where the desired compounds (II) have an acidic group such as —COOH, they may be in the form of salts with inorganic bases, such as sodium, potassium, calcium, magnesium and ammonia, or with organic bases, such as trimethylamine.

Several methods of producing the compounds (II) which are novel according to the invention are described below.

The methods of production described in the following are applicable not only to the production of the desired compounds (II) themselves [inclusive of those compounds which fall within the scope of the compounds (II) but are usable as the starting materials for the production of other compounds which also fall within the scope of the compounds (II)] but also to the production of salts thereof such as mentioned above. In the following description, however, the compounds (II) and salts thereof are collectively referred to as "compounds (II)" for short.

The compounds (II) can be produced, for example, by reacting a compound of the formula

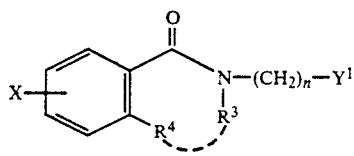
(III)

wherein $R^3$, $R^4$, n and X are as defined above and $Y^1$ is a leaving group, such as halogen or alkyl- or arylsulfonyloxy, with a compound of the formula

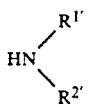
(IV)

wherein $R^{1'}$ and $R^{2'}$ are as defined above, or a salt thereof. The alkyl group or cyclic unsaturated hydrocarbon residue included in the definition of $R^{1'}$, $R^{2'}$ and $R^3$, examples of which have been given hereinabove, is generally serviceable as the alkyl or aryl moiety of said alkyl- or arylsulfonyl group represented by $Y^1$. As the salt of the compound of formula (IV), there may be mentioned acid addition salts such as mentioned above for the desired compounds (II). The above reaction is carried out in the presence or absence of a solvent and preferably in the presence or absence of a base.

Usable as the base are inorganic bases, such as sodium carbonate, potassium carbonate, lithium carbonate, sodium hydroxide, potassium hydroxide, sodium methoxide, sodium ethoxide and sodium hydride, and organic bases, such as pyridine, 4-dimethylaminopyridine and triethylamine. When a solvent is used, said solvent may be selected suitably from among lower alcohols, such as methanol, ethanol, propanol, isopropanol, n-butanol and t-butanol, ethers, such as dioxane, ether and tetrahydrofuran, aromatic hydrocarbons, such as toluene, benzene and xylene, amides, such as dimethylformamide, dimethylacetamide and hexamethylphosphoramide, esters, such as ethyl acetate and butyl acetate, and other solvents which will not interfere with the reaction. The reaction can be carried out under cooling (0° C. to 10° C.), at room temperature (11° C. to 40° C.) or with heating (41° C. to 120° C.), and the reaction period is generally 10 minutes to 48 hours, preferably 2 to 6 hours. The compound (III) is generally used in an amount of 0.3 to 5.0 moles per mole of the compound (IV). When a base is used, it is used in an amount of an approximately equimolar to or in excess of the compound (IV), preferably in an amount of 1.1 to 5 moles per mole of the compound (IV). Furthermore, if desired, the reaction may be carried out in the presence of an iodine compound, such as sodium iodide, potassium iodide or lithium iodide. When the reaction is carried out in the presence of such an iodine compound, the iodine compound is used generally in an amount of 1 to 5 moles, preferably 1.1 to 1.5 moles, per mole of the compound (IV).

The compound of the above formula (III) can be produced by a known method, for example the method described in Acta Chimica Academiae Scientiarum Hungricae, 32, 121 (1962) or Acta Chimica Academiae Scientiarum Hungricae, 39, 391 (1963), or a modification thereof.

The compounds (II) can also be produced, for example, by reacting a compound of the formula

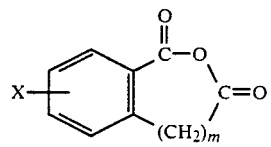
(V)

wherein X and m are as defined above, with a compound of the formula $$H_2N-(CH_2)_n-NR^{1'}R^{2'} \quad (VI)$$

wherein n, $R^{1'}$ and $R^{2'}$ are as defined above, or a salt thereof in a per se known manner. As the salt of the compound of formula (VI), there may be mentioned acid addition salts such as mentioned with respect to the compounds (II). This reaction does not always require a solvent. When a solvent is used, however, it may be any of those solvents which are in general use. Thus, for example such an organic solvent as chloroform, dichloroethane, benzene, toluene, acetonitrile, dioxane, dimethylformamide, butanol, acetic acid or acetic anhydride can be used. The reaction is carried out generally at 20° C. to 200° C., preferably at 40° C. to 150° C. In certain cases, however, heating is not always necessary. The reaction period is generally 30 minutes to °hours, preferably 2 to 8 hours. The compound (V) is used generally in an amount of ⅔ to 1.5 moles per mole of the compound (VI), preferably in an equimolar amount relative to the compound (VI).

The compound (VI) mentioned above can be produced by a known method, for example by the method described in Roczniki Chemii, 43, 1083 (1969) or Farmaco (Pavia), Edizione Scientifica, 12, 551 (1957), or a modification thereof.

Furthermore, the compounds (II) can be produced by reducing a compound of the formula $$NC-(CH_2)_{1-1}-NH^{1'}R^{2'} \quad (VII)$$

wherein n, $R^1$ and $R^2$ are as defined above, or a salt thereof by a per se known method and then reacting the resulting compound of formula (VI) with a compound of formula (V). As the salt of the compound (VII), there may be mentioned acid addition salts such as mentioned above for the compounds (II).

As the per se known method of reducing the compound (VII) to the corresponding compound (VI), there may be mentioned, for example, the method described in Chemical and Pharmaceutical Bulletin (Tokyo), 15, 228 (1967), Zhurnal obshchei Khimii, 33, 192

(1963) or Congres des Sciences Pharmaceutiques, 294, (1959).

The compound of the above formula (II) can be produced by a per se known method, for example by the method described in Congres des Sciences Pharmaceutiques, 294 (1959) or Chemical and Pharmaceutical Bulletin (Tokyo), 15, 228 (1967), or a modification thereof.

Among the compounds (II) according to the invention, those in which X is $NH_2$ can also be produced by reducing the corresponding compounds in which X is $NO_2$ [hereinafter referred to as "compounds (II: X=$NO_2$)" for short] or salts thereof. The reduction can be carried out by a per se known method, for example by the method described in Journal of Organic Chemistry, 26, 4145 (1961), Journal of the American Chemical Society, 77, 3844 (1955) or Journal of the Chemical Society, 1952, 2102, or a modification thereof.

Said reaction can be carried out, for example, in the manner of catalytic reduction in a hydrogen stream at ordinary temperature and ordinary pressure in the presence of a catalyst (e.g. palladium-carbon, platinum dioxide, Raney nickel). As the solvent, there may be mentioned, for example, methanol, ethanol, water, dimethylformamide and dioxane. Any other solvents which will not interfere with said reaction may also be used. If desired, this reaction can be carried out in the presence of an inorganic acid, such as hydrochloric acid, hydrobromic acid or sulfuric acid, or an organic acid, such as acetic acid, formic acid, propionic acid or oxalic acid.

Those compounds (II) in which X is an acylamino group (e.g. acetylamino, benzoylamino, benzenesulfonylamino) can be produced by subjecting the corresponding compounds (II: X=$NH_2$) to acylation. Such acylation can be effected, for example, by reacting the compounds (II: X=$NH_2$) with an acylating agent, such as an acid (e.g. acetic acid, propionic acid, benzoic acid, benzenesulfonic acid, p-toluenesulfonic acid), a $C_{1-4}$ alkyl ester (e.g. methyl acetate, ethyl propionate, methyl benzenesulfonate), an acid halide (e.g. acetyl chloride, acetyl bromide, p-toluenesulfonyl chloride, benzylsulfonyl chloride), and acid anhydride (e.g. acetic anhydride, propionic anhydride, benzoic anhydride) or an N-hydroxydiacylimide ester (e.g. N-acetyloxysuccinimide, N-benzoyloxyphthalimide, N-acetyloxy-5-norbornene-2,3-dicarboximide).

The acylation reaction can be carried out generally in an organic solvent, such as a hydrocarbon solvent (e.g. pentane, hexane, benzene, toluene), a halogenated hydrocarbon solvent (e.g. dichloromethane, chloroform, dichloroethane, carbon tetrachloride), an ether solvent (e.g. ethyl ether, tetrahydrofuran, dioxane, dimethoxyethene), an ester solvent (e.g. ethyl acetate, butyl acetate, methyl propionate), an amide solvent (e.g. dimethylformamide, dimethylacetamide, hyxamethylphosphoramide) or dimethyl sulfoxide, under cooling ($-10°$ C. to $10°$ C.), at room temperature ($11°$ C. to $40°$ C.) or with heating ($41°$ C. to $120°$ C.), and the reaction period required is generally 10 minutes to 12 hours. The above-mentioned acylating agent is used preferably in an amount of 1.0 to 3.0 equivalents relative to the compound (II: X=$NH_2$). Furthermore, if desired, this reaction may be carried out in the presence of an acid activating agent, such as carbonyldiimidazole, dicyclohexylcarbodiimide, diethyl cyanophosphate or diphenylphosphoryl azide, when the acylating agent is an acid, or in the presence of an organic base, such as pyridine, 4-dimethylaminopyridine, triethylamine, diisopropylamine, triethylenediamine or tetramethylethylenediamine, or an inorganic base, such as sodim hydrogen carbonate, potassium hydrogen carbonate, lithium hydrogen carbonate, potassium carbonate, sodium carbonate, lithium carbonate, lithium hydroxide, potassium hydroxide or sodium hydroxide, when the acylating agent is a $C_{1-4}$ alkyl ester or an acid halide, or in the presence of an inorganic acid, such as hydrochloric acid, hydrobromic acid, sulfuric acid, nitric acid or phosphoric acid, or an organic acid, such as acetic acid, formic acid, propionic acid, methanesulfonic acid or p-toluenesulfonic acid, when the acylating agent is an acid anhydride.

When the acylating agent is an N-hydroxydiacylimide ester, the acylation is preferably carried out in a solvent such as dichloromethane, tetrahydrofuran, dioxane, chloroform, dimethylformamide, acetonitrile or water. If desired, this reaction may be carried out in the presence of an organic or inorganic base such as mentioned above. The reaction temperature is generally $-10°$ C. to $110°$ C., preferably $0°$ C. to $30°$ C., and the reaction period is generally 5 minutes to 12 hours, preferably 30 minutes to 2 hours.

Still further, the compounds (II) can be produced, for example, by reacting a compound of the formula

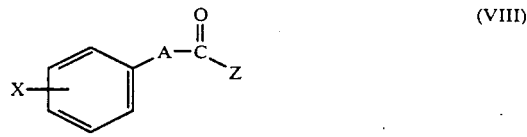

wherein A and X are as defined above and Z is a hydroxy group or a reactive group of carboxy, with a compound of the formula (VI) given above or a salt thereof.

The above-mentioned reactive group of carboxy as represented by Z is, for example, a halogen atom (e.g. chlorine, bromine, iodine), a lower ($C_{1-4}$) alkoxy group (e.g. methoxy, ethoxy, propoxy, butoxy) or an N-hydroxydiacylimide ester (e.g. N-hydroxysuccinimide ester, N-hydroxyphthalimide ester, N-hydroxy-5-norbornene-2,3-dicarboximide ester).

The reaction can be carried out generally in an organic solvent, such as a hydrocarbon solvent (e.g. pentane, hexane, benzene, toluene), a halogenated hydrocarbon solvent (e.g. dichloromethane, chloroform, dichloroethane, carbon tetrachloride), an ether solvent (e.g. ethyl ether, tetrahydrofuran, dioxane, dimethoxyethane), an ester solvent (e.g. ethyl acetate, butyl acetate, methyl propionate), an amide solvent (e.g. dimethylformamide, dimethylacetamide, hexamethylphosphoramide) or dimethyl sulfoxide, under cooling ($-10°$ C. to $10°$ C.), at room temperature ($11°$ C. to $40°$ C.) or with heating ($41°$ C. to $120°$ C.). The reaction period is generally 10 minutes to 12 hours. The compound (VI) is used preferably in an amount of 1.0 to 3.0 equivalents relative to the compound (VIII). If desired, the reaction can be carried out in the presence of an acid activating agent such as carbonyldiimidazole, dicyclohexylcarbodiimide, diethyl cyanophosphate or diphenylphosphoryl azide when Z is hydroxy, or in the presence of an organic base, such as pyridine, 4-dimethylaminopyridine, triethylamine, diisopropylamine, triethylenediamine or tetramethylethylenediamine, or an inorganic base, such as sodium hydrogen carbonate, potassium hydrogen carbonate, lithium hydrogen carbonate, potassium carbonate, sodium carbonate, lithium carbonate, lithium hydroxide, potassium hydroxide, sodium hydroxide or lithium hydride, when Z is halogen or lower alkoxy.

Furthermore, when Z is an N-hydroxydiacylimide ester, the reaction is preferably carried out in a solvent such as dichloromethane, tetrahydrofuran, dioxane, chloroform, dimethylformamide, acetonitrile or water. If necessary, this reaction is carried out in the presence of such an organic or inorganic base as mentioned above. The reaction temperature is generally −10° C. to 110° C., preferably 0° C. to 30° C., and the reaction period is generally 5 minutes to 12 hours, preferably 30 minutes to 2 hours.

The compound (VIII: Z=hydroxy) mentioned above [namely carboxylic acid] can be produced readily by hydrolyzing the corresponding compound (VIII: Z=lower alkoxy) [namely ester] by a per se known method, for example with an alkali metal hydroxide (e.g. potassium hydroxide, lithium hydroxide, sodium hydroxide), an alkali metal carbonate (e.g. potassium carbonate, sodium carbonate, lithium carbonate), an inorganic acid (e.g. hydrochloric acid, sulfuric acid, nitric acid, phosphoric acid, perchloric acid, hydroiodic acid) or an organic acid (e.g. acetic acid, propionic acid, trifluoroacetic acid, monochloroacetic acid, trichloroacetic acid, methanesulfonic acid, ethanesulfonic acid, p-toluenesulfonic acid). Any solvent in general use may be used in carrying out the hydrolysis. For example, water, lower ($C_{1-4}$) alkanols (e.g. methanol, ethanol, propanol, butanol), dioxane, tetrahydrofuran and dimethylformamide are preferred. The reaction temperature is generally about −10° C. to 120° C., preferably 0° C. to 80° C., and the reaction period is generally 10 minutes to 24 hours, preferably 30 minutes to 6 hours.

The compound (VIII: Z=halogen) can be produced by halogenating the compound (VIII: Z=hydroxy) [namely carboxylic acid] by a per se known method, for example with a halogenating agent (e.g. phosphorus oxychloride, phosphorus oxybromide, phosphorus pentachloride, phosphorus pentabromide, thionyl chloride, thionyl bromide, sulfuryl chloride, oxalyl chloride, cyanuric chloride, boron tribromide, hydrogen iodide). The acid halide obtainable by this halogenation includes acid chloride, acid bromide, acid fluoride and acid iodide, and the acid chloride and acid bromide are particularly preferred.

The above halogenation is carried out without using any solvent or in a solvent in common use. As the solvent, such inert solvents as chloroform, dichloromethane, dichloroethane, benzene and toluene are preferred.

The compound (VIII: Z=N-hydroxydiacylimide ester) can be produced by reacting the compound (VIII: Z=hydroxy) with an N-hydroxy-dicarboxylic acid imide (e.g. N-hydroxysuccinimide, N-hydroxyphthalimide, N-hydroxy-5-norbornene-2,3-dicarboximide) by a per se known method in the presence of dicyclohexylcarbodiimide. The reactin is carried out in a solvent in general use (e.g. tetrahydrofuran, dioxane, dimethylformamide, acetonitrile, water), and the comound (VIII: Z=N-hydroxydiacylimide ester) can be submitted to the next reaction step without isolation.

Among the compounds (II), those compounds (II: $R^3=R^5$, $R^4=H$) [wherein $R^5$ has the same meaning as $R^3$ defined above except for hydrogen, namely $R^5$ is a hydrocarbon residue or an acyl group, each of which may optionally be substituted] can be produced, for example, by introducing a hydrocarbon residue into or acylating the compounds (II: $R^3=R^4=H$).

Thus, for example, they can be produced by reacting the compounds (II: $R^3=R^4=H$) with a compound of the formula

$$R^5-Y^2 \qquad (IX)$$

wherein $R^5$ has the same meaning as $R^3$ defined above except for hydrogen, namely $R^5$ is a hydrocarbon residue or an acyl group, each of which may optionally be substituted, and $Y^2$ is a halogen atom when $R^5$ is a hydrocarbon residue, which may optionally be substituted, or $Y^2$ is a hydroxy group, an $OR^5$ group or a reactive group of carboxy when $R^5$ is an acyl group, by a per se known method.

The reaction of the compounds (II: $R^3=R^4=H$) with the compound (IX) does not always require the use of a solvent. When a solvent is used, however, the use of such an organic solvent as a hydrocarbon solvent (e.g. pentane, hexane, benzene, toluene), a halogenated hydrocarbon solvent (e.g. dichloromethane, chloroform, dichloroethane, carbon tetrachloride), an ether solvent (e.g. ethyl ether, tetrahydrofuran, dioxane, dimethoxyethane), an amide solvent (e.g. dimethylformamide, hexamethylphosphoramide) or dimethyl sulfoxide is generally recommendable. The reaction can be carried out at a temperature between −10° C. and 200° C., preferably between 0° C. and 120° C. The reaction period is generally 5 minutes to 12 hours, preferably 10 minutes to 6 hours. The compound (IX) is generally used in an amount equimolar to or in excess of each of the compounds (II: $R^3=R^4=H$), preferably in an amount of 1.1 to 10 moles per mole of the latter. When $R^5$ is a hydrocarbon residue, which may optionally be substituted, and $Y^2$ is a halogen atom, this reaction may be carried out, as desired, in the presence of an organic base, such as pyridine, 4-dimethylainopyridine, triethylamine, diisopropylamine, triethylenediamine or tetramethylethylenediamine, or an inorganic base, such as sodium hydride, metallic sodium, potassium amide, sodium hydrogen carbonate, potassium hydrogen carbonate, sodium carbonate, potassium carbonate, lithium hydroxide, potassium hydroxide or sodium hydroxide. Such base is used generally in an amount equimolar to or in excess of the compounds (II: $R^3=R^4=H$), preferably in an amount of 1.1 to 5 moles per mole of the latter. When $R^5$ is an acyl group, the reactive group of carboxy as represented by $Y^2$ is a halogen atom (e.g. chlorine, bromine, iodine), a lower ($C_{1-4}$) alkoxy group (e.g. methoxy, ethoxy, propoxy, butoxy) or an N-hydroxydiacylimide ester (e.g. N-hydroxysuccinimide ester, N-hydroxyphthalimide ester, N-hydroxy-5-norbornene-2,3-dicarboximide ester), for instance.

In cases where $R^5$ is an acyl group, the reaction between the compounds (II: $R^3=R^4=H$) and the compound (IX) may be carried out, if desired, in the presence of an acid activating agent, such as carbonyldiimidazole, dicyclohexylcarbodiimide, diethyl cyanophosphate or diphenylphosphoryl azide, when $Y^2$ is hydroxy, or in the presence of an inorganic acid, such as hydrochloric acid, sulfuric acid, nitric acid or phosphoric acid, an organic acid, such as acetic acid, formic acid, propionic acid, methanesulfonic acid or p-toluenesulfonic acid, or an acyl halide having the same acyl moiety as $R^5$ when $Y^2$ is $OR^5$, or in the presence of an organic base, such as pyridine, 4-dimethylaminopyridine, triethylamine, diisopropylamine, triethylenediamine or tetramethylethylenediamine, or an inorganic base, such as sodium hydrogen carbonate, potassium hydrogen carbonate, lithium hydrogen carbonate, potassium carbonate, sodium carbonate, lithium carbonate, lithium hydroxide, potassium hydroxide or sodium hydroxide, when $Y^2$ is halogen or lower alkoxy.

Furthermore, when $Y^2$ is an N-hydroxydiacylimide ester, the reaction is preferably carried out in a solvent such as dichloromethane, tetrahydrofuran, dioxane, chloroform, dimethylformamide, acetonitrile or water. If desired, this reaction may be carried out in the presence of such an organic or inorganic base as mentioned above for the case where $Y^2$ is halogen or lower alkoxy.

When the reaction is carried out in the presence of the above-mentioned acid activating agent, acid, halide or base, each is used generally in an amount equimolar to or in excess of the compounds (II: $R^3=R^4=H$), preferably in an amount of 1.1 to 5 moles per mole of the latter.

The objective compounds (II) thus produced can be isolated and purified by a known means such as filtration, extraction chromatography, recrystallization. When the compounds (II) are obtained in free from, they can be converted to their salts by the conventional method and when they are obtained in the form of their salt, they can be converted to their free form in the conventional manner.

The compounds (I) and (II) according to the invention act on the central nervous system of mammals and have potent cholinesterase inhibiting activity, and show good antiamnestic activity against various amnesia-inducing factors in humans and animals (e.g. mice).

As compared with physostigmine, the compounds (II) according to the invention are characterized in that their action on the central nervous system is very distinctly discriminated from the action on the peripheral nervous system, namely, it shows excellent selectivity between the action on the central nervous system and that on the peripheral nervous system, that they show no effects on the peripheral nervous system, such as convulsant, sialagogic and diarrhea-inducing effects at doses at which they exhibit antiamnestic activities, or, even if produced, such effects on the peripheral nervous system are very slight, that the duration of their action is long and that they have low toxicity. They can produce significant effects when they are administered orally.

Therefore, the compounds according to the invention are useful as cerebral function improving agents for mammals, including humans.

As the target diseases for which the compounds according to the invention are effective, there may be mentioned, for example, senile dementia, Alzheimer's disease, Huntington's chorea, hyperkinesia and mania, and said compounds can be used in the prevention or treatment of such diseases.

The compounds according to the invention can be administered to mammals, inclusive of humans, orally or non-orally in various dosage forms, such as tablets, granules, capsules, injections and suppositories. The pharmaceutical compositions in these dosage forms can be prepared using conventionally pharmaceutically acceptable carriers and diluents by the conventional method. The dose may vary depending on the kind of target disease, symptom and other factors but, in the case of oral administration, the daily dose is generally about 0.001 mg to 100 mg, preferably about 0.01 to 30 mg, most preferably about 0.3–10 mg per adult human.

The following working examples, reference examples, dosage form examples and test example illustrate the invention in further detail. They are, however, by no means limitative of the scope of the invention.

In the working examples and reference examples, the elution in column chromatography was performed under observation by means of TLC (thin layer chromatography), unless otherwise specified. In said TLC observation, Merck $60F_{254}$ plates were used as the TLC plates, the same solvent systems as used for the elution in column chromatography were used as the developing solvents, and a UV detector was used as the means of detection. Furthermore, the spots on the TLC plates were sprayed with 48% HBr, then heated for hydrolysis, further sprayed with a ninhydrin reagent solution and again heated for color change into a red to purplish red color. The detection method based on such phenomenon was also utilized for the identification and collection of eluate fractions containing each desired product. Unless otherwise specified, Merck Kieselgel 60 (70–230 mesh) was used as the silica gel for column chromatography.

The term "ordinary temperature" or "room temperature" as used herein generally means a temperature of about 5° C. to 40° C., and "ordinary pressure" means a pressure of about 1 atmosphere.

Unless otherwise specified, "%" is "% weight".

The following abbreviations are sometimes used below: Et:ethyl group, Me:methyl group, Pr:n-propyl group, i-Pr: i-propyl group, Ph:phenyl group, Ac:acetyl group

REFERENCE EXAMPLE 1

2-(4-Bromobutyl)-5-nitro-1H-isoindole-1,3(2H)-dione

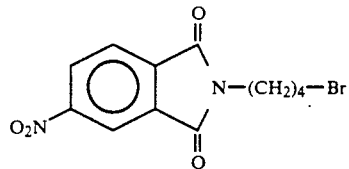

To a solution of 9.6 g of 4-nitrophthalimide in 50 ml of dimethylformamide was added slowly 1.26 g of sodium hydride, and the mixture was stirred at 60° C. for 30 minutes. A solution of 22 g of dibromobutane in 50 ml of acetone was added to the reaction mixture, and the whole mixture was heated under reflux for 16 hours. The mixture was then allowed to cool, the precipitate was removed, the solvents were distilled off under reduced pressure, and the residual solid was recrystallized from dichloromethane-ether (1:10, v/v) to give 14.7 g of white crystals having a melting point of 95°–96° C.

Elemental analysis Calculated for $C_{12}H_{11}BrN_2O_4$: C, 44.06; H, 3.39; N, 8.56; Found: C, 44.01; H, 3.20; N, 8.42.

REFERENCE EXAMPLE 2

The compounds shown in Table 1 were obtained in the same manner as in Reference Example 1.

TABLE 1

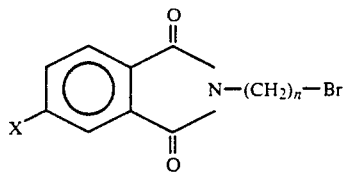

| Compound No. | X | n | Melting point (°C.) | Molecular formula | Elemental analysis Calculated (Found) | | |
|---|---|---|---|---|---|---|---|
| | | | | | C | H | N |
| 1 | $NO_2$ | 3 | 103–104 | $C_{11}H_9BrN_2O_4$ | 42.20 | 2.90 | 8.95 |
| | | | | | (42.05 | 2.79 | 8.81) |
| 2 | $NO_2$ | 5 | 78–79 | $C_{13}H_{13}BrN_2O_4$ | 45.77 | 3.84 | 8.21 |
| | | | | | (45.58 | 3.78 | 7.99) |
| 3 | $NO_2$ | 6 | 83–85 | $C_{14}H_{15}BrN_2O_4$ | 47.34 | 4.26 | 7.89 |
| | | | | | (47.09 | 4.22 | 7.63) |
| 4 | $NO_2$ | 7 | 73–74 | $C_{15}H_{17}BrN_2O_4$ | 48.80 | 4.64 | 7.59 |
| | | | | | (48.96 | 4.60 | 7.76) |

REFERENCE EXAMPLE 3

N-Benzyl-N-methyl-1,4-butanediamine dihydrochloride

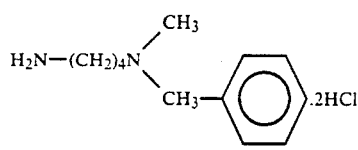

A solution of 11 g of 2-[4-(N-benzyl-N-methyl)aminobutyl]-1H-isoindole-1,3(2H)-dione hydrochloride and 5 ml of hydrazine monohydrate in 150 ml of ethanol was heated under reflux for 30 minutes. The reaction mixture was allowed to cool, the precipitate was removed, the solvent was distilled off under reduced pressure, and the residual oil was allowed to stand overnight at room temperature. The resultant precipitate was removed. To the oil thus obtained was added 20.5 ml of 3N ethanolic hydrochloric acid, and the solvent was removed under reduced pressure. The residual oil was recrystallized from ethanol-ether (1:10, v/v) to give 7.9 g of colorless crystals having a melting point of 100°–103° C.

Elemental analysis Calculated for $C_{12}H_{20}N_2.2HCl$: C, 54.34; H, 8.36; N, 10.56; Found: C, 54.11; H, 8.21; N, 10.38.

REFERENCE EXAMPLE 4

N-(3-Cyanopropyl)benzylamine hydrochloride

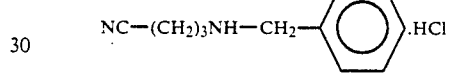

A solution of 4.0 g of 4-chlorobutyronitrile, 4.14 g of benzylamine, 7.1 g of potassium iodide and 5.9 g of potassium carbonate in 40 ml of n-butanol was heated under reflux for 6 hours. The reaction mixture was allowed to cool, 200 ml of water was added thereto, and the product was extracted with dichloromethane. The dichloromethane solution was washed with water and dried over anhydrous sodium sulfate, and the solvent was then distilled off. To the residual oil was added 13 ml of 3N ethanolic hydrochloric acid. The resultant crude crystals were collected and recrystallized from methanol-ether (1:10, v/v) to give 3.5 g of colorless crystals having a melting point of 165°–168° C.

Elemental analysis Calculated for $C_{11}H_{14}N_2.HCl$: C, 62.70; H, 7.18; N, 13.30; Found: C, 62.44; H, 6.96; N, 13.24.

REFERENCE EXAMPLE 5

The compounds shown in Table 2-(1) were obtained in the same manner as in Reference Example 4.

TABLE 2-(1)

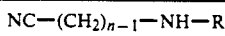

| Compound No. | n | R | Melting point (°C.) | Molecular formula | Elemental analysis Calculated (Found) | | |
|---|---|---|---|---|---|---|---|
| | | | | | C | H | N |
| 1 | 4 | 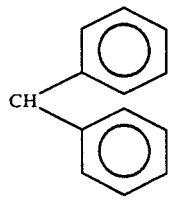 | 185–188 | $C_{17}H_{18}N_2.HCl$ | 71.19 | 6.68 | 9.77 |
| | | | | | (70.96 | 6.51 | 9.52) |

TABLE 2-(1)-continued

NC—(CH$_2$)$_{n-1}$—NH—R

| Compound No. | n | R | Melting point (°C.) | Molecular formula | Elemental analysis Calculated (Found) | | |
|---|---|---|---|---|---|---|---|
| | | | | | C | H | N |
| 2 | 4 | 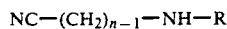 (naphthylmethyl) | 150–154 | C$_{15}$H$_{16}$N$_2$·HCl | 69.09 (68.91 | 6.57 6.37 | 10.74 10.61) |
| 3 | 4 | (adamantylmethyl) | 190–194 | C$_{15}$H$_{24}$H$_2$·HCl | 67.02 (66.89 | 9.37 9.33 | 10.42 10.34) |

REFERENCE EXAMPLE 6

The compounds shown in Table 2-(2) were obtained in the same manner as in Reference Example 3.

TABLE 2-(2)

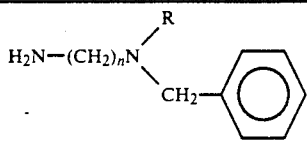

| Compound No. | n | R | Melting point (°C.) | Molecular formula | Elemental analysis Calculated (Found) | | |
|---|---|---|---|---|---|---|---|
| | | | | | C | H | N |
| 1 | 4 | Et | Oil | C$_{13}$H$_{22}$N$_2$ | 75.68 (75.62 | 10.75 10.68 | 13.58 13.55) |
| 2 | 5 | Me | " | C$_{13}$H$_{22}$N$_2$ | 75.68 (75.49 | 10.75 10.58 | 13.58 13.42) |
| 3 | 5 | Et | " | C$_{14}$H$_{24}$N$_2$ | 76.31 (76.25 | 10.98 10.91 | 12.71 12.65) |
| 4 | 5 | i-Pr | " | C$_{15}$H$_{26}$N$_2$ | 76.87 (76.68 | 11.18 11.03 | 11.95 11.71) |
| 5 | 5 | Pr | " | C$_{15}$H$_{26}$N$_2$ | 76.87 (76.83 | 11.18 11.14 | 11.95 11.91) |
| 6 | 6 | Et | " | C$_{15}$H$_{26}$N$_2$ | 76.87 (76.79 | 11.18 11.02 | 11.95 11.88) |
| 7 | 3 | Et | " | C$_{12}$H$_{20}$N$_2$ | 74.95 (74.81 | 10.48 10.33 | 14.57 14.32) |
| 8 | 7 | Et | " | C$_{16}$H$_{28}$N$_2$ | 77.36 (77.09 | 11.36 11.10 | 11.28 11.06) |

REFERENCE EXAMPLE 7

N-[(2-methoxyphenyl)methyl]-N-ethyl-1,5-pentanediamine

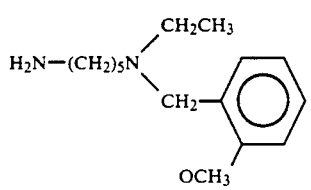

The desired compound was obtained as a colorless oil, in the same manner as in Reference Example 3.

Elemental Analysis for C$_{15}$H$_{26}$N$_2$O: Calculated C 71.96 H 10.47 N 11.19 Found C 71.79 H 10.31 N 11.00.

EXAMPLE 1

2-[4-(N-Benzyl-N-methyl)aminobutyl]-5-nitro-1H--isoindole-1,3(2H)-dione hydrochloride

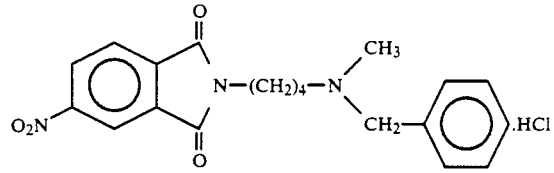

A mixture of 0.8 g of 2-[4-(N-bromobutyl)-5-nitro-1H-isoindole-1,3(2H)-dione of Reference Example 1 and a solution of 0.6 g of N-methylbenzylamine in 15 ml of toluene was stirred at 100° C. for 6 hours. The resultant precipitate was removed by filtration, and the solvent was distilled off under reduced pressure. The residual oil was subjected to silica gel column chromatography [developing solvent: dichloromethane-ethyl acetate=5:1 (v/v)]. The solution containing the desired product was deprived of the solvent under reduced pressure, 0.9 ml of 3N ethanolic hydrochloric acid was added, and the solvent was distilled off under reduced pressure. The remaining solid was recrystallized from ethanol-ether (1:5, v/v) to give 0.6 g of colorless crystals showing a melting point of 188°–192° C.

Elemental analysis Calculated for C$_{20}$H$_{21}$N$_3$O$_4$·HCl: C, 59.48; H, 5.49; N, 10.40; Found: C, 59.23; H, 5.38; N, 10.53.

EXAMPLE 2 p The compounds shown in Table 3-(1) were obtained in the same manner as in Example 1.

TABLE 3-(1)

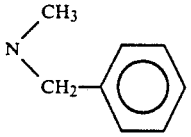

| Compound No. | X | n | NR¹R² | Melting point (°C.) | Molecular formula | Elemental analysis Calculated (Found) | | |
|---|---|---|---|---|---|---|---|---|
| | | | | | | C | H | N |
| 1 | $NO_2$ | 3 | 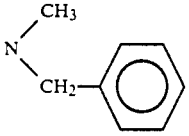 | 156–159 | $C_{19}H_{19}N_3O_4 \cdot HCl$ | 58.54 (58.28 | 5.17 4.92 | 10.78 10.93) |
| 2 | $NO_2$ | 5 | 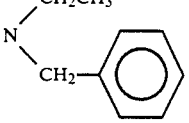 | 199–202 | $C_{21}H_{23}N_3O_4 \cdot HCl$ | 60.36 (60.17 | 5.79 5.55 | 10.06 10.26) |
| 3 | $NO_2$ | 4 | 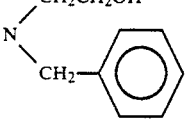 | amorphous powder | $C_{21}H_{23}N_3O_4 \cdot HCl$ | 60.36 (60.09 | 5.79 5.72 | 10.06 9.89) |
| 4 | $NO_2$ | 4 | 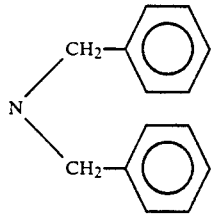 | amorphous powder | $C_{21}H_{23}N_3O_5 \cdot HCl$ | 58.13 (57.98 | 5.58 5.49 | 9.68 9.42) |
| 5 | $NO_2$ | 4 | 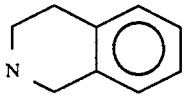 | 202–204 | $C_{26}H_{25}N_3O_4 \cdot HCl$ | 65.07 (64.89 | 5.46 5.32 | 8.76 8.61) |
| 6 | $NO_2$ | 4 | 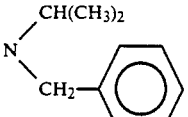 | 208–210 | $C_{21}H_{21}N_3O_4 \cdot HCl$ | 60.65 (60.46 | 5.33 5.36 | 10.10 9.93) |
| 7 | $NO_2$ | 4 | 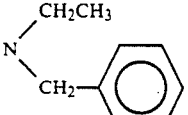 | 154–157 | $C_{22}H_{25}N_3O_4 \cdot HCl$ | 61.18 (60.98 | 6.07 6.03 | 9.73 9.52) |
| 8 | $NO_2$ | 5 |  | amorphous powder | $C_{22}H_{25}N_3O_4 \cdot HCl$ | 61.18 (60.93 | 6.07 5.91 | 9.73 9.48) |

TABLE 3-(1)-continued $$\text{structure: X-C}_6\text{H}_3(\text{COCH}_2-)_2\text{N-(CH}_2)_n-\text{NR}^1\text{R}^2 \text{ (phthalimide-type)}$$

| Compound No. | X | n | NR¹R² | Melting point (°C.) | Molecular formula | C (Calc/Found) | H (Calc/Found) | N (Calc/Found) |
|---|---|---|---|---|---|---|---|---|
| 9  | $NO_2$ | 6 | N(CH₃)(CH₂-Ph) | 161–163 | $C_{22}H_{25}N_3O_4 \cdot HCl$ | 61.18 (61.01) | 6.07 (5.95) | 9.73 (9.49) |
| 10 | $NO_2$ | 7 | N(CH₃)(CH₂-Ph) | 97–99 | $C_{23}H_{27}N_3O_4 \cdot HCl$ | 61.95 (61.92) | 6.33 (6.28) | 9.42 (9.33) |
| 11 | $NO_2$ | 4 | N((CH₂)₃CH₃)(CH₂-Ph) | amorphous powder | $C_{23}H_{27}N_3O_4 \cdot HCl$ | 61.95 (61.81) | 6.33 (6.23) | 9.42 (9.39) |
| 12 | $NO_2$ | 5 | N(CH(CH₃)₂)(CH₂-Ph) | amorphous powder | $C_{23}H_{27}N_3O_4 \cdot HCl$ | 61.95 (61.88) | 6.33 (6.30) | 9.42 (9.37) |
| 13 | $NO_2$ | 3 | N(CH₂CH₃)(CH₂-Ph) | 143–145 | $C_{20}H_{21}N_3O_4 \cdot HCl$ | 59.48 (59.39) | 5.49 (5.31) | 10.41 (10.20) |
| 14 | $NO_2$ | 6 | N(CH₂CH₃)(CH₂-Ph) | 134–137 | $C_{23}H_{27}N_3O_4 \cdot HCl$ | 61.95 (61.85) | 6.33 (6.19) | 9.42 (9.30) |
| 15 | $NO_2$ | 7 | N(CH₂CH₃)(CH₂-Ph) | Oil | $C_{24}H_{29}N_3O_4 \cdot HCl$ | 62.67 (62.59) | 6.57 (6.53) | 9.14 (9.11) |
| 16 | $NO_2$ | 4 | N(Pr)(CH₂-Ph) | amorphous powder | $C_{22}H_{25}N_3O_4 \cdot HCl$ | 61.18 (61.10) | 6.07 (5.99) | 9.73 (9.69) |
| 17 | $NO_2$ | 5 | N(Et)(CH₂-C₆H₄-Me) | amorphous powder | $C_{23}H_{27}N_3O_4 \cdot HCl$ | 61.95 (61.81) | 6.33 (6.14) | 9.42 (9.38) |
| 18 | $NO_2$ | 5 | N(Et)(CH₂-C₆H₄-OMe) | oil | $C_{23}H_{27}N_3O_5 \cdot HCl$ | 59.80 (59.68) | 6.11 (6.01) | 9.10 (9.06) |

TABLE 3-(1)-continued

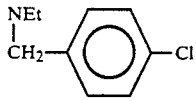

| Compound No. | X | n | NR¹R² | Melting point (°C.) | Molecular formula | Elemental analysis Calculated (Found) | | |
|---|---|---|---|---|---|---|---|---|
| | | | | | | C | H | N |
| 19 | $NO_2$ | 5 | NEt–CH₂–(4-Cl-C₆H₄) | amorphous powder | $C_{22}H_{24}ClN_3O_4 \cdot HCl$ | 56.66 (56.59 | 5.40 5.32 | 9.01 8.97) |
| 20 | $NO_2$ | 5 | NEt–CH₂–(3-Cl-C₆H₄) | 148–152 | $C_{22}H_{24}ClN_3O_4 \cdot HCl$ | 56.66 (56.61 | 5.40 5.21 | 9.01 8.88) |
| 21 | $NO_2$ | 5 | NEt–CH₂–(2-Cl-C₆H₄) | oil | $C_{22}H_{24}ClN_3O_4 \cdot HCl$ | 56.66 (56.45 | 5.40 5.36 | 9.01 8.92) |
| 22 | $NO_2$ | 5 | NEt–CH₂–(2-F-C₆H₄) | amorphous powder | $C_{22}H_{24}FN_3O_4 \cdot HCl$ | 58.73 (58.65 | 5.60 5.43 | 9.34 9.21) |
| 23 | $NO_2$ | 5 | NEt–CH₂–(2-Me-C₆H₄) | oil | $C_{23}H_{27}N_3O_4 \cdot HCl$ | 61.95 (61.89 | 6.33 6.31 | 9.42 9.36) |
| 24 | $NO_2$ | 5 | NEt–CH₂–(2-O₂N-C₆H₄) | amorphous powder | $C_{22}H_{24}H_4O_6 \cdot HCl$ | 55.41 (55.24 | 5.28 5.09 | 11.75 11.58) |
| 25 | $NO_2$ | 5 | NEt–CH₂–(2-MeO-C₆H₄) | 84–87 | $C_{23}H_{27}N_3O_5 \cdot HCl$ | 59.80 (59.77 | 6.11 6.05 | 9.10 9.02) |
| 26 | $NO_2$ | 5 | NEt–CH₂–(3-OMe-C₆H₄) | amorphous powder | $C_{23}H_{27}N_3O_5 \cdot HCl$ | 59.80 (59.65 | 6.11 6.06 | 9.10 9.04) |
| 27 | $NO_2$ | 5 | NEt–CH₂–(2,3-diOMe-C₆H₃) | amorphous powder | $C_{24}H_{29}N_3O_6 \cdot HCl$ | 58.59 (58.41 | 6.15 6.02 | 8.54 8.44) |

TABLE 3-(1)-continued

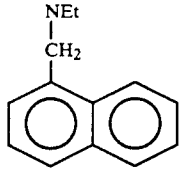

| Compound No. | X | n | NR$^1$R$^2$ | Melting point (°C.) | Molecular formula | Elemental analysis Calculated (Found) | | |
|---|---|---|---|---|---|---|---|---|
| | | | | | | C | H | N |
| 28 | NO$_2$ | 5 | NEt<br>\|<br>CH$_2$-naphthyl | amorphous powder | C$_{26}$H$_{27}$N$_3$O$_4$.HCl | 64.79<br>(64.57 | 5.86<br>5.62 | 8.72<br>8.69) |
| 29 | NO$_2$ | 5 | NEt<br>\|<br>CH$_2$-naphthyl | amorphous powder | C$_{26}$H$_{27}$N$_3$O$_4$.HCl | 64.79<br>(64.68 | 5.86<br>5.81 | 8.72<br>8.68) |

EXAMPLE 3

5-Amino-2-[4-(N-benzyl-N-methyl)aminobutyl]-1H-isoindole-1,3(2H)-dione hydrochloride

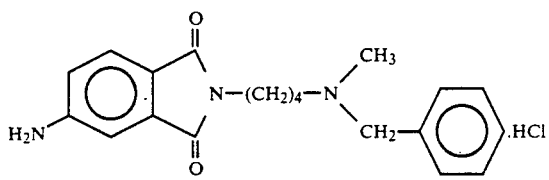

To a solution of 2.5 g of 2-[4-(N-benzyl-N-methyl)aminobutyl]-5-nitro-1H-isoindole-1,3(2H)-dione hydrochloride (obtained in Example 1) in 100 ml of ethanol were added 1 ml of 12N concentrated hydrochloric acid and 0.2 g of 10% palladium carbon, and catalytic reduction was carried out under a hydrogen gas stream at ordinary temperature and pressure. When the absorption of hydrogen was complete, the catalyst was removed and the solvent was distilled off under reduced pressure. To the oily residue was added 10% sodium hydroxide to make the pH 10, and the mixture was extracted with dichloromethane. The dichloromethane extract was dried over anhydrous sodium sulfate, the solvent was then distilled off, and the oily residue was subjected to silica gel column chromatography [developing solvent: ethyl acetate-methanol=20:1 (v/v)]. The solvent was removed from the eluate fractions containing the desired product under reduced pressure. To the thus-obtained oily residue was added 2 ml of 3N ethanolic hydrochloric acid, the solvent was then distilled off, and the remainder solid was recrystallized from ethanol-ether (1:5, v/v) to give 1.8 g of yellow crystals having a melting point of 114°-117° C.

Elemental analysis Calculated for C$_{20}$H$_{23}$N$_3$O$_2$.HCl: C, 64.25; H, 6.47; N, 11.24; Found: C, 63.98; H, 6.54; N, 11.02.

EXAMPLE 4

2-[4-(N-Benzyl-N-methyl)aminobutyl]-5-benzoylamino-1H-isoindole-1,3(2H)-dione

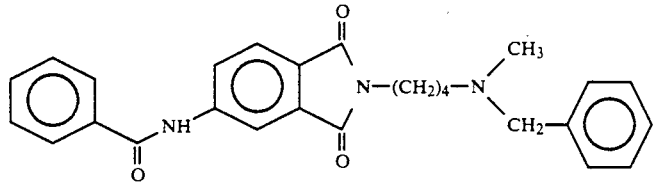

A solution of 0.5 g of 5-amino-2-[4-(N-benzyl-N-methyl)aminobutyl]-1H-isoindole-1,3(2H)-dione hydrochloride (obtained in Example 3) and 0.2 g of benzoyl chloride in 5 ml of pyridine was stirred at room temperature for 1 hour. Thereafter, water was added to the reaction mixture, and the whole mixture was extracted with dichloromethane. The dichloromethane solution was washed with water and dried over anhydrous sodium sulfate, and the solvent was then distilled off. The oily residue was crystallized from hexane to give 0.53 g of colorless crystals having a melting point of 118°-119° C.

Elemental analysis Calculated for C$_{27}$H$_{27}$N$_3$O$_3$: C, 73.45; H, 6.16; N, 9.52; Found: C, 73.21; H, 6.05; N, 9.36.

EXAMPLE 5

The compounds shown in Table 3-(2) were obtained in the same manner as in Example 4.

TABLE 3-(2)

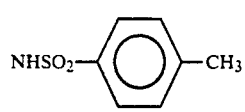

| Compound No. | X | Melting point (°C.) | Molecular formula | Elemental analysis Calculated (Found) | | |
|---|---|---|---|---|---|---|
| | | | | C | H | N |
| 1 | NHCOCH₃ | 128–129 | C₂₂H₂₅N₃O₃ | 69.64 (69.34 | 6.64 6.52 | 11.70 10.83) |
| 2 | NHSO₂—⟨benzene⟩—CH₃ | amorphous powder | C₂₇H₂₉N₃O₄S·HCl | 61.41 (61.24 | 5.73 5.67 | 7.96 7.71) |
| 3 | NHSO₂CH₂—⟨benzene⟩ | amorphous powder | C₂₇H₂₉N₃O₄S·HCl | 61.41 (61.18 | 5.73 5.74 | 7.96 7.64) |

EXAMPLE 6

2-[4-(N-Benzyl-N-methyl)aminobutyl]-1,3(2H)-dioxoisoindole-5-carboxylic acid hydrochloride

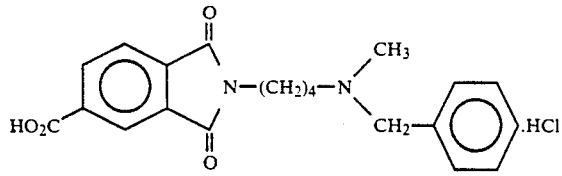

A solution of 1.0 g of N-benzyl-N-methyl-1,4-butanediamine dihydrochloride (obtained in Reference Example 3) and 0.72 g of trimellitic anhydride in 20 ml of acetic acid-dimethylformamide (1:1, v/v]was heated under reflux for 6 hours. Thereafter, the solvent was distilled off under reduced pressure, and the oily residue was subjected to silica gel column chromatography [developing solvent: dichloromethane-ethanol=5:1 (v/v)]. The solvent was distilled off from the fractions containing the desired product under reduced pressure, 1.25 ml of 3N ethanolic hydrochloric acid was added to the residue, and the solvent was removed under reduced pressure The solid residue was recrystallized from ethanol-ether to give 0.4 g of colorless crystals having a melting point of 204°–207° C.

Elemental analysis Calculated for C₂₁H₂₂N₃O₄·HCl: C, 60.50; H, 5.56; N, 10.08; Found: C, 60.41; H, 5.33; N, 9.81.

EXAMPLE 7

2-[4-(N-benzyl)amino]-5-nitro-1H-isoindole-1,3(2H)dione hydrochloride

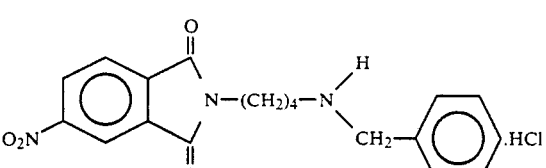

(1) To a suspension of 1.1 g of lithium aluminum hydride in 50 ml of tetrahydrofuran was added slowly 2.9 g of N-(3-cyanopropyl)benzylamine (obtained in Reference Example 4) at room temperature. The reaction mixture was heated gently under reflux for 15 minutes and then allowed to cool. To the mixture was added dropwise and carefully 2.2 ml of water and then 1.8 ml of 10% aqueous sodium hydroxide. The resultant precipitate was filtered off, the filtrate was dried over anhydrous sodium sulfate and the solvent was distilled off under reduced pressure to give 1.7 g of N-benzyl-1,4-butanediamine as a colorless oil.

(2) The procedure of Example 6 was followed using 1.7 g of N-benzyl-1,4-butanediamine [obtained in step (1)] and 1.8 g of 4-nitrophthalic anhydride to give 2.0 g of 2-[4-(N-benzyl)aminobutyl]-5-nitro-1H-isoindole-1,3(2H)dione hydrochloride as colorless crystals having a melting point of 244°–246° C.

Elemental analysis Calculated for C₁₉H₁₉N₃O₄·HCl: C, 58.54; H, 5.17; N, 10.78; Found: C, 58.29; H, 5.03; N, 10.53.

EXAMPLE 8

The compounds shown in Table 3-(3) were obtained in the same manner as in Example 6 or 7.

TABLE 3-(3)

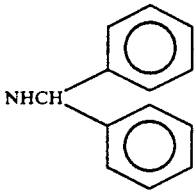

| Compound No. | X | n | NR¹R² | Melting point (°C.) | Molecular formula | Elemental analysis Calculated (Found) | | |
|---|---|---|---|---|---|---|---|---|
| | | | | | | C | H | N |
| 1 | 5-$NO_2$ | 4 |  | 221–223 | $C_{25}H_{23}N_3O_4 \cdot HCl$ | 64.45 (64.27 | 5.19 5.24 | 9.02 8.91) |
| 2 | 5-$NO_2$ | 4 | 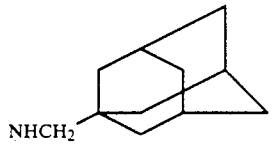 | 215–217 | $C_{23}H_{21}N_3O_4 \cdot HCl$ | 62.80 (62.62 | 5.04 4.99 | 9.55 9.37) |
| 3 | 5-$NO_2$ | 4 | NHCH₂-[adamantyl] | 218–220 | $C_{23}H_{29}N_3O_4 \cdot HCl$ | 61.67 (61.64 | 6.75 6.67 | 9.38 9.33) |

EXAMPLE 9

(E)-N-[4-(N-Methyl-N-benzyl)aminobutyl]-3-(4-nitrophenyl)-2-propenamide

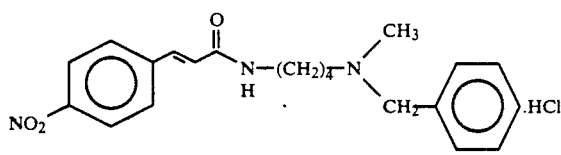

To an ice-cooled solution of 1.43 g of (E)-4-nitrocinnamic acid, 2.1 g of N-benzyl-N-methyl-1,4-butanediamine dihydrochloride (Reference Example 3) and 3.7 ml of triethylamine in 20 ml of dimethylformamide was added 1.8 g of diethyl cyanophosphate. The mixture was stirred with ice cooling for 1 hour and, then, 100 ml of water was added. The product was extracted with dichloromethane, the dichloromethane solution was dried over anhydrous sodium sulfate, and the solvent was then distilled off under reduced pressure. The oily residue was subjected to silica gel column chromatography [developing solvent: ethyl acetate-methanol=20:1 (v/v)], the solvent was distilled off from the fractions containing the desired product, 2.4 ml of 3N ethanolic hydrochloric acid was added to the residue, and the solvent was distilled off to give 2.3 g of hygroscopic amorphous powder.

Elemental analysis Calculated for $C_{21}H_{25}N_3O_3 \cdot HCl$: C, 62.45; H, 6.49; N, 10.40; Found: C, 62.39; H, 6.22; N, 10.15.

EXAMPLE 10

5-Amino-2-[5-(N-benzyl-N-ethyl)aminopentyl]-1H-isoindole-1,3(2H)-dione dihydrochloride

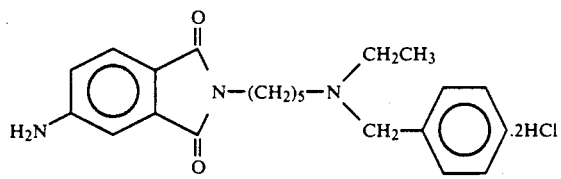

Yellow amorphous powder was obtained in the same manner as in Example 3.

Elemental analysis Calculated for $C_{22}H_{27}N_3O_2 \cdot 2HCl$: C, 60.28; H, 6.67; N, 9.59; Found: C, 60.22; H, 6.59; N, 9.43.

EXAMPLE 11

The compounds shown in Table 3-(4) were obtained in the same manner as in Example 4.

TABLE 3-(4)

Structure: 4-X-substituted phthalimide with N-(CH₂)₅-N(CH₂CH₃)(CH₂-phenyl)

| Compound No. | X | Melting point (°C.) | Molecular formula | Elemental analysis Calculated (Found) | | |
|---|---|---|---|---|---|---|
| | | | | C | H | N |
| 1 | NHCOCH₃ | 120–121 | C₂₄H₂₉N₃O₃ | 70.74 (70.68 | 7.17 7.01 | 10.31 10.19) |
| 2 | NHCO-phenyl | 125–126 | C₂₉H₃₁N₃O₃ | 74.18 (74.17 | 6.65 6.58 | 8.95 8.90) |
| 3 | NHCOCH₂-phenyl | 129–132 | C₃₀H₃₃N₃O₃ | 74.51 (74.45 | 6.88 6.76 | 8.69 8.52) |
| 4 | NHSO₂-C₆H₄-CH₃ | 109–112 | C₂₉H₃₃N₃O₄S | 67.03 (66.93 | 6.40 6.33 | 8.09 7.92) |
| 5 | NHSO₂CH₂-phenyl | 54–57 | C₂₉H₃₃N₃O₄S | 67.03 (66.89 | 6.40 6.41 | 8.09 8.06) |
| 6 | NHSO₂CH₃ | 94–96 | C₂₃H₂₉N₃O₄S | 62.28 (62.03 | 6.59 6.44 | 9.47 9.41) |

EXAMPLE 12

The compounds shown in Table 3-(5) were obtained in the same manner as in Example 6.

TABLE 3-(5)

Structure: X-substituted phthalimide with N-(CH₂)ₙ-N(R¹)(CH₂-phenyl), positions labeled 4,5,6,7

| Compound No. | n | R¹ | X | Melting point (°C.) | Molecular formula | Elemental analysis Calculated (Found) | | |
|---|---|---|---|---|---|---|---|---|
| | | | | | | C | H | N |
| 1 | 4 | CH₃ | 4-NO₂ | 170–171 | C₂₀H₂₁N₃O₄·HCl | 59.48 (59.41 | 5.49 5.38 | 10.41 10.35) |
| 2 | 4 | CH₃ | 5-Cl | 208–210 | C₂₁H₂₁N₃O₄·HCl | 60.65 (60.57 | 5.33 5.19 | 10.10 9.95) |
| 3 | 5 | C₂H₅ | 4-NO₂ | amorphous powder | C₂₂H₂₅N₃O₄·HCl | 61.18 (61.12 | 6.07 6.01 | 9.73 9.66) |
| 4 | 5 | C₂H₅ | 5-OH | amorphous powder | C₂₂H₂₆N₂O₄·HCl | 65.58 (65.55 | 6.75 6.69 | 6.95 6.94) |
| 5 | 5 | C₂H₅ | 5-OCOCH₃ | amorphous powder | C₂₄H₂₈N₂O₄·HCl | 64.79 (64.73 | 6.57 6.47 | 6.30 6.11) |
| 6 | 5 | C₂H₅ | 5-OCH₃ | amorphous powder | C₂₃H₂₈N₂O₃·HCl | 66.26 (66.21 | 7.01 6.93 | 6.72 6.63) |
| 7 | 5 | C₂H₅ | 5-Cl | amorphous powder | C₂₂H₂₅ClN₂O₂·HCl | 62.71 (62.64 | 6.22 6.09 | 6.65 6.48) |
| 8 | 5 | C₂H₅ | 5-CO₂H | amorphous powder | C₂₃H₂₆N₂O₄·HCl | 64.11 (64.06 | 6.32 6.27 | 6.50 6.39) |
| 9 | 5 | C₂H₅ | 5-CON(C₂H₅)₂ | Oil | C₂₇H₃₅N₃O₃·HCl | 66.72 (66.64 | 7.47 7.41 | 8.65 8.57) |

TABLE 3-(5)-continued

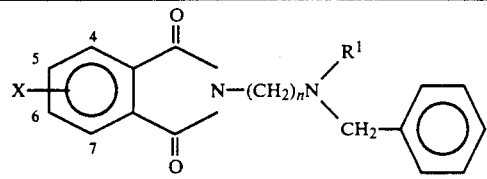

| Compound No. | n | R¹ | X | Melting point (°C.) | Molecular formula | Elemental analysis Calculated (Found) | | |
|---|---|---|---|---|---|---|---|---|
| | | | | | | C | H | N |
| 10 | 5 | $C_2H_5$ | 5-COPh | amorphous powder | $C_{29}H_{30}N_2O_3.HCl$ | 70.94 (70.91) | 6.36 (6.33) | 5.71 (5.64) |
| 11 | 5 | $C_2H_5$ | 5-$CH_3$ | Oil | $C_{23}H_{28}N_2O_2.HCl$ | 68.90 (68.81) | 7.29 (7.25) | 6.99 (6.91) |
| 12 | 5 | Et | 5-$OSO_2CH_3$ | amorphous powder | $C_{23}H_{28}N_2O_5S.HCl$ | 57.43 (57.33) | 6.08 (6.01) | 5.82 (5.75) |
| 13 | 5 | Et | 5-$CONHCH_3$ | 93–95 | $C_{24}H_{29}N_3O_3$ | 70.74 (70.59) | 7.17 (7.02) | 10.31 (10.22) |

EXAMPLE 13

Methyl 2-[5-(N-benzyl-N-ethyl)aminopentyl]-1,3(2H)-dioxo-1H-isoindole-5-carboxylate hydrochloride

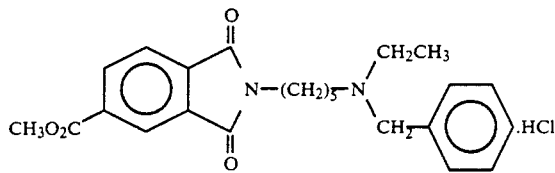

To a solution of 0.7 g of 2-[5-(N-benzyl-N-ethyl)aminopentyl]-1,3-dioxo-1H-isoindole-5-carboxylic acid hydrochloride (Compound No. 8 obtained in Example 12) in 30 ml of methanol was added 3 drops of acetyl chloride, and the mixture was heated under reflux for 2 hours. Thereafter, the methanol was distilled off, the oily residue was dissolved in dichloromethane, the solution was washed with 10% sodium hydroxide and then with water and dried over anhydrous sodium sulfate, and the solvent was distilled off. The oily residue was subjected to silica gel column chromatography [developing solvent: dichloromethane-ethanol=20:1 (v/v)], and the solvent was removed from the fractions containing the desired product under reduced pressure. To the oil obtained was added 0.5 ml of 3N ethanolic hydrochloric acid, and the solvent was distilled off to give 0.64 g of an oil.

Elemental analysis Calculated for $C_{24}H_{28}N_2O_4.HCl$: C, 64.79; H, 6.57; N, 6.30; Found: c, 64.67; h, 6.56; n, 6.25.

EXAMPLE 14

The compounds shown in Table 3-(6) were obtained in the same manner as in Example 9.

TABLE 3-(6)

| Compound No. | n | R¹ | X | Melting point (°C.) | Molecular formula | Elemental analysis Calculated (Found) | | |
|---|---|---|---|---|---|---|---|---|
| | | | | | | C | H | N |
| 1 | 4 | Me | 3-$NO_2$ | 184–185 | $C_{21}H_{25}N_3O_3.HCl$ | 62.45 (62.28) | 6.49 (6.38) | 10.40 (10.31) |
| 2 | 4 | Me | 2-$NO_2$ | 134–135 | $C_{21}H_{25}N_3O_3.HCl$ | 62.45 (62.39) | 6.49 (6.42) | 10.40 (10.36) |
| 3 | 5 | Me | 4-$NO_2$ | amorphous powder | $C_{22}H_{27}N_3O_3.HCl$ | 63.23 (63.17) | 6.75 (6.71) | 10.05 (9.98) |
| 4 | 5 | Et | 4-$NO_2$ | amorphous powder | $C_{23}H_{29}N_3O_3.HCl$ | 63.95 (63.81) | 7.00 (6.91) | 9.73 (9.63) |
| 5 | 5 | i-Pr | 4-$NO_2$ | amorphous powder | $C_{24}H_{31}N_3O_3.HCl$ | 64.64 (64.47) | 7.23 (7.11) | 9.42 (9.31) |
| 6 | 5 | Pr | 4-$NO_2$ | amorphous powder | $C_{24}H_{31}N_3O_3.HCl$ | 64.64 (64.61) | 7.23 (7.22) | 9.42 (9.38) |
| 7 | 4 | Et | 4-$NO_2$ | amorphous powder | $C_{22}H_{27}N_3O_3.HCl$ | 63.23 (63.14) | 6.75 (6.59) | 10.05 (10.03) |
| 8 | 6 | Et | 4-$NO_2$ | amorphous powder | $C_{24}H_{31}N_3O_3.HCl$ | 64.64 (64.63) | 7.23 (7.17) | 9.42 (9.40) |
| 9 | 3 | Et | 4-$NO_2$ | 70–72 | $C_{21}H_{25}N_3O_3$ | 68.64 (68.51) | 6.86 (6.79) | 11.44 (11.34) |
| 10 | 7 | Et | 4-$NO_2$ | amorphous powder | $C_{25}H_{33}N_3O_3.HCl$ | 65.28 (65.03) | 7.45 (7.19) | 9.14 (9.06) |

TABLE 3-(6)-continued

| Compound No. | n | R¹ | X | Melting point (°C.) | Molecular formula | Elemental analysis Calculated (Found) | | |
|---|---|---|---|---|---|---|---|---|
| | | | | | | C | H | N |
| 11 | 5 | Et | 3-OMe, 4-OMe | amorphous powder | $C_{25}H_{34}N_2O_3 \cdot HCl$ | 67.17 (67.08 | 7.89 7.76 | 6.27 6.05) |
| 12 | 5 | Et | 2-$NO_2$ | amorphous powder | $C_{23}H_{29}N_3O_3 \cdot HCl$ | 63.95 (63.81 | 7.00 6.94 | 9.73 9.56) |
| 13 | 5 | Et | 3-$NO_2$ | amorphous powder | $C_{23}H_{29}N_3O_3 \cdot HCl$ | 63.95 (63.77 | 7.00 6.83 | 9.73 9.62) |
| 14 | 5 | Et | 4-Cl | amorphous powder | $C_{23}H_{29}ClN_2O \cdot HCl$ | 65.56 (65.29 | 7.18 7.01 | 6.65 6.45) |
| 15 | 5 | Et | 4-$CH_3$ | amorphous powder | $C_{24}H_{32}N_2O \cdot HCl$ | 71.89 (71.66 | 8.30 8.09 | 6.99 6.85) |
| 16 | 5 | Et | 4-CN | amorphous powder | $C_{24}H_{29}N_3O \cdot HCl$ | 69.97 (69.74 | 7.34 7.17 | 10.20 10.03) |

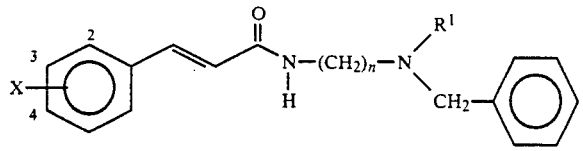

| 17 | 5 | Et | 4-OH | amorphous powder | $C_{23}H_{30}N_2O_2 \cdot HCl$ | 68.56 (68.33 | 7.75 7.58 | 6.95 6.71) |
|---|---|---|---|---|---|---|---|---|
| 18 | 5 | Et | 4-OMe | amorphous powder | $C_{24}H_{32}N_2O_2 \cdot HCl$ | 69.13 (69.00 | 7.98 7.83 | 6.72 6.59) |
| 19 | 5 | Et | 3-OMe | amorphous powder | $C_{24}H_{32}N_2O_2 \cdot HCl$ | 69.13 (69.04 | 7.98 7.94 | 6.72 6.67) |
| 20 | 5 | Et | 4-SMe | amorphous powder | $C_{24}H_{32}N_2OS \cdot HCl$ | 66.57 (66.41 | 7.68 7.55 | 6.47 6.38) |
| 21 | 5 | Et | 4-SOMe | amorphous powder | $C_{24}H_{32}N_2O_2S \cdot HCl$ | 64.19 (64.07 | 7.41 7.32 | 6.24 6.13) |
| 22 | 5 | Et | 4-$SO_2$Me | amorphous powder | $C_{24}H_{32}N_2O_3S \cdot HCl$ | 61.99 (61.85 | 7.15 7.03 | 6.02 5.97) |
| 23 | 5 | Et | 3-OMe, 4-OMe, 5-OMe | amorphous powder | $C_{26}H_{36}N_2O_4 \cdot HCl$ | 65.46 (65.42 | 7.82 7.73 | 5.87 5.85) |
| 24 | 5 | Et | 3-OH, 4-$NO_2$ | amorphous powder | $C_{23}H_{29}N_3O_4 \cdot HCl$ | 61.67 (61.48 | 6.75 6.59 | 9.38 9.16) |
| 25 | 5 | Et | 3-$NO_2$, 4-Cl | amorphous powder | $C_{23}H_{28}ClN_3O_3 \cdot HCl$ | 59.23 (59.00 | 6.27 6.05 | 9.01 8.93) |

EXAMPLE 15

(E)-N-Acetyl-N-[4-(N-methyl-N-benzyl-)aminobutyl]-3-(4-nitrophenyl)-2-propenamide hydrochloride

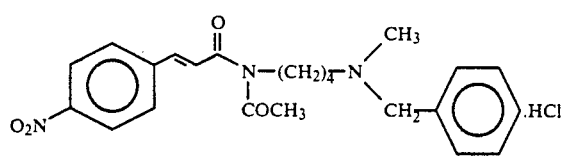

A catalytic amount of p-toluenesulfonic acid monohydrate was added to a solution of 0.4 g of (E)-N-[4-(N-methyl-N-benzyl)aminobutyl]-3-(4-nitrophenyl)-2-propenamide (Example 9) in 5 ml of acetic anhydride, and the mixture was heated at 80° C with stirring for 8 hours and then allowed to cool. Water (50 ml) was added to the mixture and the product was extracted with dichloromethane. The dichloromethane solution was dried over anhydrous sodium sulfate, and the solvent was then distilled off under reduced pressure. The oily residue was subjected to column chromatography [developing solvent: ethyl acetate-ethanol=20:1 (v/v)], the solvent was distilled off from the fractions containing the desired product, 0.4 ml of 3N ethanolic hydrochloric acid was added to the residue, and the solvent was distilled off to give 0.43 g of amorphous powder.

Elemental analysis Calculated for $C_{23}H_{27}N_3O_4 \cdot HCl$: C, 61.95; H, 6.33; N, 9.42; Found: C, 61.88; H, 6.30; N, 9.39.

EXAMPLE 16

The compounds shown in Table 3-(7) were obtained in the same manner as in Example 15.

TABLE 3-(7)

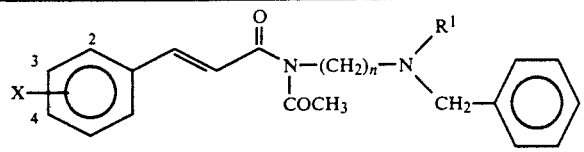

| Compound No. | n | R¹ | X | Melting point (°C.) | Molecular formula | Elemental analysis Calculated (Found) | | |
|---|---|---|---|---|---|---|---|---|
| | | | | | | C | H | N |
| 1 | 4 | Et | 4-$NO_2$ | amorphous powder | $C_{24}H_{29}N_3O_4 \cdot HCl$ | 62.67 (62.58) | 6.57 6.50 | 9.14 9.07) |
| 2 | 5 | Et | 4-$NO_2$ | amorphous powder | $C_{25}H_{31}N_3O_4 \cdot HCl$ | 63.35 (63.31) | 6.80 6.77 | 8.87 8.85) |
| 3 | 6 | Et | 4-$NO_2$ | amorphous powder | $C_{26}H_{33}N_3O_4 \cdot HCl$ | 63.99 (63.87) | 7.02 6.93 | 8.61 8.43) |
| 4 | 5 | Et | 3-$NO_2$ | oil | $C_{25}H_{31}N_3O_4 \cdot HCl$ | 63.35 (63.19) | 6.80 6.57 | 8.87 8.61) |
| 5 | 5 | Et | 4-Cl | amorphous powder | $C_{25}H_{31}ClN_2O_2 \cdot HCl$ | 64.79 (64.53) | 6.96 6.88 | 6.05 5.87) |
| 6 | 5 | Et | 4-CN | amorphous powder | $C_{26}H_{31}N_3O_2 \cdot HCl$ | 68.78 (68.56) | 7.10 6.97 | 9.26 9.21) |
| 7 | 5 | Et | 3-OMe | oil | $C_{26}H_{34}N_2O_3 \cdot HCl$ | 68.03 (67.85) | 7.69 7.48 | 6.10 5.93) |
| 8 | 5 | Et | 4-$SO_2CH_3$ | amorphous powder | $C_{26}H_{34}N_2O_4S \cdot HCl$ | 61.58 (61.47) | 6.96 6.89 | 5.52 5.41) |
| 9 | 5 | Et | 3-OH, 4-$NO_2$ | amorphous powder | $C_{25}H_{31}N_3O_5 \cdot HCl$ | 61.28 (61.15) | 6.58 6.41 | 8.58 8.41) |
| 10 | 5 | Et | 3-OAc, 4-$NO_2$ | amorphous powder | $C_{27}H_{33}N_3O_6 \cdot HCl$ | 60.95 (60.82) | 6.44 6.36 | 7.89 7.77) |
| 11 | 5 | Et | 3-$NO_2$, 4-Cl | amorphous powder | $C_{25}H_{30}ClN_3O_4 \cdot HCl$ | 59.06 (58.96 | 6.15 6.03 | 8.26 8.09) |

EXAMPLE 17

Ethyl 2-[5-(N-benzyl-N-ethyl)aminopentyl]-1,3(2H)-dioxo-1H-isoindole-5-carboxylate.hydrochloride

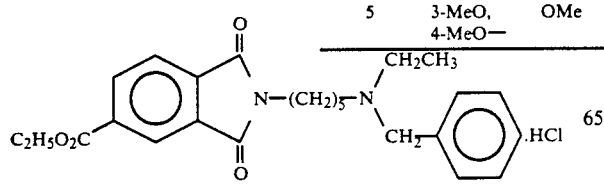

The objective compound was obtained, as colorless oily substance, in the same manner as in Example 13.

Elemental analysis Calculated for $C_{25}H_{30}N_2O_4 \cdot HCl$: C, 65.42; H, 6.81; N, 6.10, Found: C, 65.31; H, 6.63; N, 6.03.

EXAMPLE 18

The compounds shown in Table 3-(8) were obtained in the same manner as in Example 9.

TABLE 3-(8)

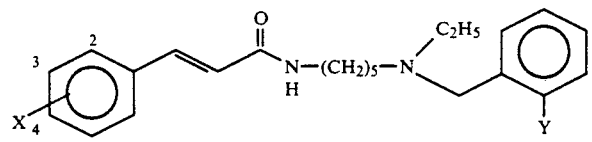

| Compound No. | X | Y | Melting Point (°C.) | Molecular Formula | Elemental Analysis Calculated (Found) | | |
|---|---|---|---|---|---|---|---|
| | | | | | C | H | N |
| 1 | 3-$NO_2$, 4Cl | OMe | Amorphous powder | $C_{24}H_{30}ClN_3O_4 \cdot HCl$ | 58.07 (57.86) | 6.29 6.07 | 8.46 8.34) |
| 2 | 4-$NO_2$ | OMe | " | $C_{24}H_{31}N_3O_4 \cdot HCl$ | 62.40 (62.16) | 6.98 6.83 | 9.10 9.01) |
| 3 | 4-$SO_2CH_3$ | OMe | " | $C_{25}H_{34}N_2O_4S \cdot HCl$ | 60.65 (60.47) | 7.13 7.02 | 5.66 5.46) |
| 4 | 4-CN | OMe | " | $C_{25}H_{31}N_3O_2 \cdot HCl$ | 67.94 (67.79) | 7.30 7.02 | 9.51 9.35) |
| 5 | 3-MeO, 4-MeO— | OMe | " | $C_{26}H_{36}N_2O_4 \cdot HCl$ | 65.46 (65.31) | 7.82 7.66 | 5.87 5.79) |

EXAMPLE 19

The compounds shown in Table 3-(9) were obtained in the same manner as in Example 15.

TABLE 3-(9)

$$\text{X}\underset{4}{\overset{3}{-}}\underset{}{\underset{}{\text{C}_6\text{H}_3}}\underset{2}{-}\text{CH=CH-C(=O)-N(R}^3\text{)-(CH}_2\text{)}_5\text{-N(C}_2\text{H}_5\text{)-CH}_2\text{-C}_6\text{H}_4\text{-Y}$$

| Compound No. | X | R³ | Y | Melting Point (°C.) | Molecular Formula | Elemental Analysis Calculated (Found) | | |
|---|---|---|---|---|---|---|---|---|
| | | | | | | C | H | N |
| 1 | 4-NO₂ | COC₂H₅ | H | Oil | C₂₆H₃₃N₃O₄.HCl | 63.99 (63.71 | 7.02 6.89 | 8.61 8.50) |

EXAMPLE 20

The compounds shown in Table 3-(10) were obtained in the same manner as in Example 3.

TABLE 3-(10)

$$\text{X}\underset{4}{\overset{3}{-}}\underset{}{\underset{}{\text{C}_6\text{H}_3}}\underset{2}{-}\text{CH=CH-C(=O)-N(R}^3\text{)-(CH}_2\text{)}_5\text{-N(CH}_2\text{CH}_3\text{)-CH}_2\text{-C}_6\text{H}_5$$

| Compound No. | X | R³ | Melting Point (°C.) | Molecular Formula | Elemental Analysis Calculated (Found) | | |
|---|---|---|---|---|---|---|---|
| | | | | | C | H | N |
| 1 | 3-NH₂ | H | Amorphous powder | C₂₃H₃₁N₃O.2HCl | 63.01 (62.91 | 7.59 7.43 | 9.58 9.39) |
| 2 | 3-NH₂ | COCH₃ | " | C₂₅H₃₃N₃O₂.2HCl | 62.50 (62.38 | 7.34 7.16 | 8.75 8.62) |
| 3 | 4-NH₂ | H | " | C₂₃H₃₁N₃O.2HCl | 63.01 (62.97 | 7.59 7.52 | 9.58 9.44) |

EXAMPLE 21

The compounds shown in Table 3-(11) were obtained in the same manner as in Example 4.

TABLE 3-(11)

$$\text{X}\underset{4}{\overset{3}{-}}\underset{}{\underset{}{\text{C}_6\text{H}_3}}\underset{2}{-}\text{CH=CH-C(=O)-N(R}^3\text{)-(CH}_2\text{)}_5\text{-N(C}_2\text{H}_5\text{)-CH}_2\text{-C}_6\text{H}_5$$

| Compound No. | X | R³ | Melting Point (°C.) | Molecular Formula | Elemental Analysis Calculated (Found) | | |
|---|---|---|---|---|---|---|---|
| | | | | | C | H | N |
| 1 | 3-NHCOCH₃ | COCH₃ | Amorphous powder | C₂₇H₃₅N₃O₃.HCl | 66.72 (66.54 | 7.47 7.35 | 8.65 8.49) |
| 2 | 4-NHCOCH₃ | H | " | C₂₅H₃₃N₃O₂.HCl | 67.63 (67.58 | 7.72 7.61 | 9.46 9.29) |

DOSAGE FORM EXAMPLE 1

| | |
|---|---|
| (1) 2-[4-(N-Benzyl-N-methyl)aminobutyl]-5-nitro-1H-isoindole-1,3(2H)-dione hydrochloride | 1 g |
| (2) Lactose | 197 g |
| (3) Corn starch | 50 g |
| (4) Magnesium stearate | 2 g |

The components (1) and (2) and 20 g of corn starch were mixed up together and the mixture was granulated together with a paste prepared from 15 g of corn starch and 25 ml of water. To the granulation product were added 15 g of corn starch and the component (4), and the mixture was compressed on a compression tableting machine to give 2,000 tablets each containing 0.5 mg of the component (1) and having a diameter of 3 mm.

DOSAGE FORM EXAMPLE 2

| | |
|---|---|
| (1) 2-[4-(N-Benzyl-N-methyl)aminobutyl]-5-nitro-1H-isoindole-1,3(2H)-dione hydrochloride | 2 g |
| (2) Lactose | 196 g |
| (3) Corn starch | 50 g |
| (4) Magnesium stearate | 2 g |

The components (1) and (2) and 20 g of corn starch were mixed up together and the mixture was granulated together with a paste prepared from 15 g corn starch and 25 ml of water. To the granulation product were added 15 g of corn starch and the component (4), and the mixture was compressed on a compression tableting machine to give 2,000 tablets each containing 1 mg of the component (1) and having a diameter of 5 mm.

TEST EXAMPLE

--- Acetylchlolinesterase inhibiting activity ---

The compounds according to the invention were examined for cholinesterase inhibiting activity using (acetyl-[$^3$H])-acetylcholine. Thus, the S1 fraction of a male Wistar rat cerebral cortex homogenate was used as a cholinesterase source, and (acetyl-[$^3$H])-acetylcholine (as substrate) and each test compound according to the invention were added and, after 30 minutes of incubation, the reaction was terminated. A toluene type scintillator was added, and the mixture was shaken, whereby the reaction product [$^3$H]-acetic acid was transferred to the toluene layer. The cholinesterase activity was determined by counting said [$^3$H]-acetic acid with a liquid scintillation counter.

The cholinesterase inhibiting activity of each test compound was expressed in terms of 50% inhibitory concentration ($IC_{50}$). The anticholinesterase activity of physostigmine was also determined by the same method. The results thus obtained are shown in Table 4.

TABLE 4

| Compound (Example No.) | Acetylcholinesterase inhibiting activity $IC_{50}$ ($\mu M$) |
|---|---|
| 1 | 9.5 |
| 2-2 | 1.4 |
| 2-3 | 0.25 |
| 2-4 | 1.5 |
| 2-6 | 18 |
| 2-7 | 0.49 |
| 2-8 | 0.15 |
| 2-9 | 0.48 |
| 2-10 | 1.8 |
| 2-11 | 1.9 |
| 2-12 | 0.83 |
| 2-13 | 10 |
| 2-14 | 0.66 |
| 2-15 | 4.6 |
| 2-16 | 1.9 |
| 2-17 | 0.37 |
| 2-18 | 0.27 |
| 2-19 | 0.24 |
| 2-20 | 0.24 |
| 2-21 | 0.13 |
| 2-22 | 0.27 |
| 2-23 | 0.11 |
| 2-24 | 0.49 |
| 2-25 | 0.028 |
| 2-26 | 0.045 |
| 2-27 | 0.27 |
| 2-28 | 0.11 |
| 3 | 34 |
| 4 | 11 |
| 5-1 | 11 |
| 5-2 | 37 |

TABLE 4-continued

| Compound (Example No.) | Acetylcholinesterase inhibiting activity $IC_{50}$ ($\mu M$) |
|---|---|
| 5-3 | 9.2 |
| 8-2 | 2.9 |
| 9 | 14 |
| 10 | 1.2 |
| 11-1 | 0.32 |
| 11-2 | 0.73 |
| 11-3 | 1.5 |
| 11-4 | 2.2 |
| 11-5 | 0.24 |
| 11-6 | 0.47 |
| 12-3 | 0.68 |
| 12-4 | 2.5 |
| 12-5 | 2.1 |
| 12-6 | 0.71 |
| 12-7 | 1.3 |
| 12-8 | 8.8 |
| 12-9 | 0.98 |
| 12-10 | 1.1 |
| 12-11 | 1.8 |
| 12-12 | 0.38 |
| 12-13 | 0.38 |
| 13 | 0.58 |
| 14-1 | 13 |
| 14-2 | 18 |
| 14-4 | 3.0 |
| 14-9 | 11 |
| 14-10 | 15 |
| 14-11 | 5.4 |
| 14-12 | 3.9 |
| 14-13 | 3.0 |
| 14-14 | 16 |
| 14-15 | 16 |
| 14-16 | 5.0 |
| 14-17 | 13 |
| 14-18 | 16 |
| 14-19 | 9.3 |
| 14-20 | 21 |
| 14-21 | 7.5 |
| 14-22 | 3.2 |
| 14-23 | 4.1 |
| 14-24 | 0.17 |
| 14-25 | 1.9 |
| 15 | 19 |
| 16-1 | 7.3 |
| 16-2 | 0.56 |
| 16-3 | 3.0 |
| 16-4 | 0.53 |
| 16-5 | 2.2 |
| 16-6 | 0.46 |
| 16-7 | 5.8 |
| 16-8 | 0.17 |
| 16-9 | 0.35 |
| 16-10 | 0.28 |
| 16-11 | 0.41 |
| 17 | 0.68 |
| 18-1 | 0.22 |
| 18-2 | 0.29 |
| 18-3 | 0.23 |
| 18-4 | 0.37 |
| 18-5 | 0.43 |
| 19-1 | 4.3 |
| 20-1 | 19 |
| 20-2 | 2.4 |
| 20-3 | 10 |
| 20-1 | 1.8 |
| 21-2 | 5.7 |
| Physostigmine | 0.22 |

In the above table, the notation "Compound 2-2", for instance, stands for the compound No. 2 obtained in Example 2.

Nootropic Action

--- Effect on $CO_2$-induced ammesia in mice ---

Effect of the compounds (I) and (II) on impairment of passive avoidance response, induced by exposing mice to 100% $CO_2$ gas, was evaluated. Male ICR mice (Japan Clea) aged 5 weeks were used. The experimental apparatus consisted of two compartments, and one illuminated chamber (9×9×25 cm) was connected to dark chamber (25×25×30 cm) with a guillotine door. Each mouse was placed in the illuminated compartment and then allowed to enter the dark one. When the mouse entered the dark chamber, the door was closed and AC 0.5 mA footshock was applied to the floor grid of the dark chamber. The mouse can memorize the experience receiving the uncomfortable stimulus for a few weeks. Next, the consolidation processes of memory were disturbed by an experimental manipulation: Each mouse was placed under the hypoxic condition by being placed into a 4l desiccator filled with 100% $CO_2$ gas, immediately after receiving the footshock in the dark chamber. When his respiratory function was stopped, the mouse was taken out from the desiccator and given artificial respiration till recovering spontaneous respiration. This procedure disturbed the consolidation of the memory (experience of footshock). On the next day, a retention test was performed whether the mouse memorizes the footshock or not. In the test, the mouse was again placed in the illuminated compartment and the latency to enter the dark compartment was measured.

The mice subjected to hypoxia entered the dark compartment with short latency, 10-20 sec. The mice treated with the compound (I) showed much longer latency than the controls. The ameliorating effect of compounds on the amnesia induced by hypoxia was evaluated by the latency time, and was expressed as the percent change of the mean time of the vehicle-treated control group (Table 5.). The compounds were suspended in 5% arabic gum solution, and administered intraperitoneally (i.p.) 30 min. before the test.

TABLE 5

| Compound Exp. No. | Dose (mg/kg, i.p.) | Anti-amnesia |
|---|---|---|
| Saline | — | 100 |
| 2-8 | 3 | 326** |
| 11-1 | 1 | 455** |
| Reference Physostigmine | 0.3 | 210** |

**$p < 0.01$

General Symptoms

Four mice were used for each group. Mice were placed in stainless steel cages (13×18×25 cm) and after a 1-hr habituation period the compounds were administered. Symptoms of mice were observed for 4 hours after the compounds were administered. Peripheral and central effects of the compounds were estimated with the incidences of salivation and lachrymation, and a grade of hypothermia, respectively.

The compounds which were soluble in saline were dissolved in saline and the others were suspended in 5% arabic gum solution. Each compound was administered orally (100 mg/kg). The results are shown in Table 6.

Scorings of the symptoms were made as follows.

+++: marked
++: moderate
+: mild
—: non-detected

TABLE 6

| Compound Exp. No | Salivation | Lachrymation | Hypothermia |
|---|---|---|---|
| 2-8 | + | ++ | + |
| 11-1 | — | ++ | + |

$LD_{50}$ value Ten mice were used for each group. $LD_{50}$ value was estimated with the dose (mg/kg, p.o.) which induced death in 50% of mice. The results are shown in Table 7.

TABLE 7

| Compound Exp. No. | $LD_{50}$ (mg/kg, p.o.) |
|---|---|
| 2-8 | 300 |
| 11-1 | >300 |
| Reference Physostigmine | 2.6 |

What we claim are:
1. A compound of the formula

$$X \text{---} \underset{R_4}{\underset{|}{\overset{\overset{\displaystyle A\text{---}\overset{O}{\overset{\|}{C}}\text{---}N\text{---}(CH_2)_n\text{---}N}{}}{\text{benzene ring}}}} \begin{matrix} R^{1'} \\ \diagdown \\ \diagup \\ R^{2'} \end{matrix}$$

wherein
R$^{1'}$ is a hydrogen atom or $C_{1-4}$ alkyl group which may be substituted by a hydroxy group:
R$^{2'}$ is benzyl, naphthylmethyl, 1-phenylethyl or benzhydryl, each of which may be substituted by one to three substituents selected from the group S$^1$ consisting of
(a) halogen, nitro, nitrile, hydroxy, $C_{1-4}$ alkoxy, $C_{1-4}$ alkylthio, amino, mono- or di-$C_{4-4}$-alkyl substituted amino, $C_{1-4}$ alkoxycarbonyl, carboxy, $C_{1-6}$ alkylcarbonyl, carbamoyl, mono- or di-$C_{1-4}$ alkyl-substituted carbamoyl and adamantan-1-yl; and
(b) phenyl, naphthyl, benzoyl, phenoxycarbonyl, phenyl-$C_{1-4}$ alkylcarbamoyl or phenylcarbamoyl, wherein the substituent (b) has 0-4 further substituents on the phenyl or naphthyl group which are $C_{1-4}$ alkyl, halogen, hydroxy, benzyloxy, amino, nitro, $C_{1-4}$ alkoxycarbonyl or a phenyl which phenyl has 0-4 substituents of the group consisting of $C_{1-4}$ alkyl, $C_{1-4}$ alkoxy, halogen, hydroxy, benzyloxy, amino, mono- or di-$C_{1-4}$ alkyl substituted amino, nitro or $C_{1-4}$ alkoxycarbonyl;
R$^3$ is
(1) a hydrogen atom,
(2) a straight or branched $C_{1-11}$ alkyl, $C_{2-4}$ alkenyl, or $C_{4-4}$ alkynyl, a monocyclic $C_{3-7}$ cycloalkyl, bicyclo[3,2,1]oct-2-yl, bicyclo[3,3,1]non-2-yl, adamantan-1-yl, a phenyl or a naphthyl, each of which may be substituted by one to three substituents selected from the above defined group S$^1$, or
(3) a $C_{1-6}$ alkylcarbonyl, $C_{3-8}$ cycloalkylcarbonyl, a $C_{3-8}$ cycloalkyl-$C_{1-6}$ alkylcarbonyl, a $C_{2-6}$ alkenyl- or alkynyl-carbonyl, a benzoyl, a naphthoyl, carbamoyl, a mono- or di-$C_{1-4}$ alkylcarbamoyl, a mono or di-$C_{3-6}$ alkenyl- or alkynylcarbamoyl, phenylcarbamoyl, naphthylcarbamoyl, diphenylcarbonyl, sodiumsulfonyl, a $C_{1-6}$ alkylsulfonyl, a $C_{2-6}$ alkenyl or alkynylsulfonyl, phenylsulfonyl, naphthylsulfonyl, a $C_{1-6}$ alkyloxycarbonyl, a $C_{3-8}$ cycloalkyloxycarbonyl, a $C_{2-7}$ alkenyl or alkynyl oxycarbonyl, a phenyloxycarbonyl or a benzyloxycarbonyl, each of which may be substituted by one to three substituents selected from the above-defined group $S^1$, and $R^4$ is a hydrogen atom, or $R^3$ and $R^4$ combinedly form a group of the formula

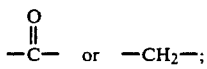

A is a bond or —CH=CH—;

X represents one substituent or two substituents selected from the group $S^3$ consisting of $C_{1-4}$ alkyl, halogen atoms, nitro, nitrile, $C_{1-4}$ alkoxy, phenoxy, $C_{1-4}$ alkylcarbonyl amino, $C_{1-4}$ alkylsulfonylamino, phenyl-$C_{1-4}$ alkylsulfonylamino, phenylsulfonylamino, $C_{1-4}$ alkylcarbonyl, $C_{1-4}$ alkoxycarbonyl, phenoxycarbonyl, benzoyl, carbamoyl, mono- or di-$C_{1-4}$ alkyl-substituted carbamoyl, phenylcarbamoyl, $C_{1-4}$ alkylthio, phenyl $C_{1-4}$ alkylthio, $C_{1-6}$ alkylsulfinyl, phenyl $C_{1-4}$ alkyl sulfinyl, $C_{1-6}$ alkylsulfonyl, phenyl-$C_{1-4}$ alkylsulfonyl, phenyl, and phenyl-$C_{1-4}$ alkyl groups; and n is an integer of 4 to 7;

or a pharmaceutically acceptable salt thereof.

2. A compound as claimed in claim 1, wherein $R^{1'}$ is ethyl and $R^{2'}$ is a benzyl group which may be substituted by methyl, methoxy, chlorine and/or fluorine, the number of the substituent(s) being one or two, or naphthylmethyl.

3. A compound as claimed in claim 1, wherein at least one of the substituent(s) represented by X is nitro.

4. A compound as claimed in claim 1, wherein n is 4 or 5.

5. A compound as claimed in claim 1, which is 2-[5-[N-ethyl-N-(2-methylphenyl)methyl]aminopentyl]-5-nitro-1H-isoindole-1,3(2H)-dione.

6. A compound as claimed in claim 1, which is 2-[5-[N-ethyl-N-(2-methoxyphenyl)methyl]aminopentyl]-5-nitro-1H-isoindole-1,3(2H)-dione.

7. A compound as claimed in claim 1, which is 2-[5-[N-ethyl-N-(1-naphthyl)methyl]aminopentyl-9 -5-nitro-1H-isoindole-1,3(2H)-dione.

8. A compound as claimed in claim 1, which is 2-[5-[N-ethyl-N-(2,3-dimethoxyphenyl)methyl]aminopentyl]-5-nitro-1H-isoindole-1,3(2H)-dione.

9. A compound as claimed in claim 1, which is 2-[5-[N-ethyl-N-(3-methoxyphenyl)methyl]aminopentyl]-5-nitro-1H-isoindole-1,3(2H)-dione.

10. A compound as claimed in claim 1
wherein X and n are defined as in claim 1 and $R^{1'}$ is a hydrogen atom or a $C_{1-4}$ alkyl group which may be substituted by a hydroxy group; and $R^{2'}$ is benzyl, naphthylmethyl, 1-phenylethyl or benzhydryl, each of which may be substituted by one to three substituents selected from the group $S^1$ as defined in claim 1, and (i) when A is a bond, $R^3$ and $R^4$ are defined as in claim 1, and (ii) when A is —CH=CH—, $R^3$ is
  (1) a hydrogen atom,
  (2) a straight or branched $C_{1-11}$ alkyl, $C_{2-4}$ alkenyl, or $C_{2-4}$ alkynyl, a monocyclic $C_{3-7}$ cycloalkyl, bicyclo[3,2,1]oct-2-yl, bicyclo[3,3,1]non-2-yl, adamantan-1-yl, a phenyl or a naphthyl, each of which may be substituted by one to three substituents selected from the $S^1$, or
  (3) a $C_{1-6}$ alkylcarbonyl, $C_{3-8}$ cycloalkylcarbonyl, a $C_{3-8}$ cycloalkyl-$C_{1-6}$ alkyl carbonyl, a $C_{2-6}$ alkenyl- or alkynyl-carbonyl, a benzoyl, a naphthoyl, carbamoyl, a mono- or di-$C_{1-4}$ alkylcarbamoyl, a mono or di-$C_{3-6}$ alkenyl- or alkynylcarbamoyl, phenylcarbamoyl, naphthylcarbamoyl, diphenyl carbamoyl; sodium sulfonate group, a $C_{1-6}$ alkylsulfonyl, a $C_{2-6}$ alkenyl or alkynylsulfonyl, phenylsulfonyl, naphthylsulfonyl, a $C_{1-6}$ alkyloxycarbonyl, a $C_{3-8}$ cycloalkyloxycarbonyl, a $C_{2-7}$ alkenyl or alkynyl oxycarbonyl, a phenyloxycarbonyl or a benzyloxycarbonyl, each of which may be substituted by one to three substituents selected from the group $S^1$, and $R^4$ is a hydrogen atom.

11. A cholinesterase inhibiting composition which contains an effective cholinesterase inhibiting amount of a compound as claimed in claim 1 and a pharmaceutically acceptable carrier or diluent.

12. An agent for inhibiting cholinesterase in a mammal in need thereof which comprises an effective cholinesterase inhibiting amount of a compound of claim 1 in a pharmaceutically acceptable carrier.

13. A pharmaceutical agent for treatment of hypoxic cerebral dysfunction which contains an effective cholinesterase inhibiting amount of a compound of claim 1 and a pharmaceutically acceptable carrier.

* * * * *